US010202569B2

(12) United States Patent
Novak et al.

(10) Patent No.: US 10,202,569 B2
(45) Date of Patent: Feb. 12, 2019

(54) RADIAL MICROFLUIDIC DEVICES AND METHODS OF USE

(71) Applicant: President and Fellows of Harvard College, Cambridge, MA (US)

(72) Inventors: Richard Novak, Jamaica Plain, MA (US); David Conegliano, Cambridge, MA (US); Liliana Teixeira, Cambridge, MA (US); Donald E. Ingber, Boston, MA (US)

(73) Assignee: PRESIDENT AND FELLOWS OF HARVARD COLLEGE, Cambridge, MA (US)

( * ) Notice: Subject to any disclaimer, the term of this patent is extended or adjusted under 35 U.S.C. 154(b) by 0 days.

(21) Appl. No.: 15/217,714

(22) Filed: Jul. 22, 2016

(65) Prior Publication Data

US 2017/0022464 A1  Jan. 26, 2017

Related U.S. Application Data

(60) Provisional application No. 62/196,539, filed on Jul. 24, 2015.

(51) Int. Cl.
| | | |
|---|---|---|
| *C12M 3/06* | (2006.01) | |
| *G01N 33/50* | (2006.01) | |
| *C12N 5/071* | (2010.01) | |
| *B01L 3/00* | (2006.01) | |

(52) U.S. Cl.
CPC ....... *C12M 23/16* (2013.01); *B01L 3/502761* (2013.01); *C12N 5/069* (2013.01); *G01N 33/5005* (2013.01); *B01L 2200/0694* (2013.01); *B01L 2300/0851* (2013.01); *B01L 2300/0877* (2013.01); *B01L 2300/0887* (2013.01); *B01L 2400/086* (2013.01)

(58) Field of Classification Search
CPC ..... A61K 35/407; C12M 23/16; C12M 23/38; C12M 25/02; C12M 21/00; C12M 29/04; C12M 35/08; C12N 2501/11; C12N 2501/12; C12N 2501/734; C12N 2533/54; C12N 5/0672; C12N 5/0634; C12N 5/069; C12N 2502/13; C12N 2502/23; C12N 2502/28; C12N 5/00; C12N 5/0636; C12N 5/0652; C12N 5/0679; C12N 5/0018; C12N 5/0075; G01N 33/5005; G01N 33/5023; G01N 33/5067; G01N 33/505; G01N 33/5088; G01N 33/50; G01N 33/5011; G01N 33/5017; G01N 33/5044; B01L 2200/0694; B01L 2300/0851; B01L 2300/0877; B01L 2300/0887; B01L 2400/086; B01L 3/502761; B01L 3/502753; B01L 2300/0581; B01L 3/502715; C07K 16/2809; C07K 16/2818
See application file for complete search history.

(56) References Cited

U.S. PATENT DOCUMENTS

| | | |
|---|---|---|
| 3,300,386 A | 1/1967 | Aron-Brunetiere |
| 3,313,290 A | 4/1967 | Chance |
| 3,722,504 A | 3/1973 | Sawyer |
| 3,941,662 A | 3/1976 | Munder |
| 3,948,732 A | 4/1976 | Haddad |
| 4,225,671 A | 9/1980 | Puchinger |
| 4,436,824 A | 3/1984 | Bishop |
| 4,446,229 A | 5/1984 | Indech |
| 4,537,860 A | 8/1985 | Tolbert |
| 4,610,878 A | 9/1986 | Wilson |
| 4,629,686 A | 12/1986 | Gruenberg |
| 4,650,766 A | 3/1987 | Harm |
| 4,673,650 A | 6/1987 | Braden |
| 4,720,462 A | 1/1988 | Rosenson |
| 4,734,372 A | 3/1988 | Rotman |
| 4,737,455 A | 4/1988 | De Baetselier |
| 4,749,654 A | 6/1988 | Karrer |
| 4,835,102 A | 5/1989 | Bell |
| 4,839,280 A | 6/1989 | Banes |
| 4,851,354 A | 7/1989 | Winston |
| 4,929,542 A | 5/1990 | Risley |
| 4,940,853 A | 7/1990 | Vandenburgh |
| 5,002,890 A | 3/1991 | Morrison |
| 5,043,260 A | 4/1991 | Jauregui |
| 5,108,926 A | 4/1992 | Klebe |

(Continued)

FOREIGN PATENT DOCUMENTS

| | | |
|---|---|---|
| WO | WO 2014/127250 | 8/2014 |
| WO | WO 2014/210364 | 12/2014 |

(Continued)

OTHER PUBLICATIONS

US 6,465,252, 10/2002, Toner (withdrawn)

(Continued)

*Primary Examiner* — Deborah K Ware
(74) *Attorney, Agent, or Firm* — Nixon Peabody LLP

(57) ABSTRACT

A microfluidic device for simulating a function or response of a tissue is disclosed. The device includes an inlet for receiving a fluid in the device, and an outlet for removing the fluid from the device. The device further includes a fluid channel in fluid communication with the inlet and the outlet for flowing the fluid through the device. The fluid channel defines a chamber well that receives cells associated with the tissue. The device also includes an interface structure between the fluid channel and the chamber well for permitting migration of at least one of cells, particulates, chemicals, molecules, liquids, or gases between the fluid within the fluid channel and the chamber well.

12 Claims, 16 Drawing Sheets

(56) References Cited

U.S. PATENT DOCUMENTS

| | | |
|---|---|---|
| 5,160,490 A | 11/1992 | Naughton |
| 5,197,575 A | 3/1993 | Mangum et al. |
| 5,217,899 A | 6/1993 | Shapiro |
| 5,290,684 A | 3/1994 | Kelly |
| 5,316,905 A | 5/1994 | Mori |
| 5,348,879 A | 9/1994 | Shapiro |
| 5,486,335 A | 1/1996 | Wilding |
| 5,496,697 A | 3/1996 | Parce |
| 5,498,392 A | 3/1996 | Wilding |
| 5,587,128 A | 12/1996 | Wilding |
| 5,612,188 A | 3/1997 | Shuler |
| 5,637,469 A | 6/1997 | Wilding |
| 5,645,432 A | 7/1997 | Jessop |
| 5,726,026 A | 3/1998 | Wilding |
| 5,744,366 A | 4/1998 | Kricka |
| 5,750,329 A | 5/1998 | Quinn |
| 5,820,769 A | 10/1998 | Chou |
| 5,900,160 A | 5/1999 | Whitesides |
| 5,906,828 A | 5/1999 | Cima |
| 6,048,723 A | 4/2000 | Banes |
| 6,054,277 A | 4/2000 | Furcht |
| 6,133,030 A | 10/2000 | Bhatia |
| 6,197,575 B1 | 3/2001 | Griffith |
| 6,255,106 B1 | 7/2001 | Marx |
| 6,306,644 B1 | 10/2001 | Marx |
| 6,329,195 B1 | 12/2001 | Pfaller |
| 6,454,924 B2 | 9/2002 | Jedrzejewski |
| 6,472,202 B1 | 10/2002 | Banes |
| 6,530,370 B1 | 3/2003 | Heinonen |
| 6,562,616 B1 | 5/2003 | Toner |
| 6,586,235 B1 | 7/2003 | Banes |
| 6,630,801 B2 | 10/2003 | Schuurmans |
| 6,645,759 B2 | 11/2003 | Banes |
| 6,653,124 B1 | 11/2003 | Freeman |
| 6,730,516 B2 | 5/2004 | Jedrzejewski |
| 6,921,253 B2 | 7/2005 | Shuler |
| 6,998,265 B2 | 2/2006 | Banes |
| 7,049,057 B2 | 5/2006 | Atala |
| 7,288,405 B2 | 10/2007 | Shuler |
| 7,314,718 B1 | 1/2008 | Dasgupta |
| 7,438,856 B2 | 10/2008 | Jedrzejewski |
| 7,745,209 B2 | 6/2010 | Martin |
| 7,763,456 B2 | 7/2010 | Li |
| 7,790,028 B1 | 9/2010 | Weinberg |
| 7,960,166 B2 | 6/2011 | Vacanti |
| 7,964,078 B2 | 6/2011 | Lee |
| 7,976,795 B2 | 7/2011 | Zhou |
| 7,977,089 B2 | 7/2011 | Wikswo |
| 7,985,336 B2 | 7/2011 | Weinberg |
| 8,030,061 B2 | 10/2011 | Shuler |
| 8,147,562 B2 | 4/2012 | Vacanti |
| 8,187,863 B2 | 5/2012 | Sim |
| 8,268,152 B2 | 9/2012 | Stelzle |
| 8,273,572 B2 | 9/2012 | Martin |
| 8,318,479 B2 | 11/2012 | Domansky |
| 8,343,740 B2 | 1/2013 | Gonda |
| 8,357,528 B2 | 1/2013 | Vacanti |
| 8,460,546 B2 | 6/2013 | Weinberg |
| 8,470,589 B2 | 6/2013 | Martin |
| 8,647,861 B2 | 2/2014 | Ingber |
| 2002/0129813 A1 | 9/2002 | Litherland |
| 2002/0173033 A1 | 11/2002 | Hammerick |
| 2003/0021792 A1 | 1/2003 | Roben |
| 2003/0082795 A1 | 5/2003 | Shuler |
| 2003/0096405 A1 | 5/2003 | Takayama |
| 2003/0175824 A1 | 9/2003 | Pishko |
| 2004/0034435 A1 | 2/2004 | Atala |
| 2004/0132166 A1 | 7/2004 | Miller |
| 2005/0032205 A1 | 2/2005 | Smith |
| 2005/0169962 A1 | 8/2005 | Bhatia |
| 2005/0266393 A1 | 12/2005 | Baxter |
| 2005/0273995 A1 | 12/2005 | Kanagasabapathi |
| 2006/0019326 A1 | 1/2006 | Vacanti |
| 2006/0099116 A1 | 5/2006 | Manger |
| 2006/0154361 A1 | 7/2006 | Wikswo |
| 2006/0263336 A1 | 11/2006 | Caplan |
| 2006/0270023 A1 | 11/2006 | LeDuc |
| 2007/0015273 A1 | 1/2007 | Shuler |
| 2007/0015274 A1 | 1/2007 | Shuler |
| 2007/0015275 A1 | 1/2007 | Shuler |
| 2007/0020693 A1 | 1/2007 | Shuler |
| 2007/0026519 A1 | 2/2007 | Shuler |
| 2007/0037273 A1 | 2/2007 | Shuler |
| 2007/0037275 A1 | 2/2007 | Shuler |
| 2007/0037277 A1 | 2/2007 | Shuler |
| 2007/0048727 A1 | 3/2007 | Shuler |
| 2007/0122794 A1 | 5/2007 | Shuler |
| 2007/0122896 A1 | 5/2007 | Shuler |
| 2007/0144514 A1 | 6/2007 | Yeates |
| 2007/0172943 A1 | 7/2007 | Freedman |
| 2007/0207194 A1 | 9/2007 | Grayburn |
| 2007/0224677 A1 | 9/2007 | Neumann |
| 2007/0243627 A1 | 10/2007 | Takayama |
| 2007/0275435 A1 | 11/2007 | Kim |
| 2007/0275455 A1 | 11/2007 | Hung |
| 2007/0275882 A1 | 11/2007 | Meijer |
| 2007/0281353 A1 | 12/2007 | Vacanti |
| 2008/0032380 A1 | 2/2008 | Kleis |
| 2008/0064088 A1 | 3/2008 | Shuler |
| 2008/0166794 A1 | 7/2008 | Shuler |
| 2008/0166795 A1 | 7/2008 | Shuler |
| 2008/0233607 A1 | 9/2008 | Yu |
| 2008/0318334 A1 | 12/2008 | Robotti |
| 2009/0028755 A1 | 1/2009 | Jedrzejewski |
| 2009/0074623 A1 | 3/2009 | Park |
| 2009/0078614 A1 | 3/2009 | Varghese |
| 2009/0131858 A1 | 5/2009 | Fissell |
| 2009/0134235 A1 | 5/2009 | Ivri |
| 2009/0220932 A1 | 9/2009 | Ingber |
| 2010/0015697 A1 | 1/2010 | Junger |
| 2010/0041128 A1 | 2/2010 | Banes |
| 2010/0043494 A1 | 2/2010 | Gascon |
| 2010/0267136 A1 | 10/2010 | Vacanti |
| 2010/0294986 A1 | 11/2010 | Sultana |
| 2010/0304355 A1 | 12/2010 | Shuler |
| 2010/0323439 A1 | 12/2010 | Takayama |
| 2011/0000482 A1 | 1/2011 | Gumaste |
| 2011/0027804 A1 | 2/2011 | Yarmush |
| 2011/0053207 A1 | 3/2011 | Hoganson |
| 2011/0086382 A1 | 4/2011 | Marx |
| 2011/0183312 A1 | 7/2011 | Huang |
| 2011/0269226 A1 | 11/2011 | Van Noort |
| 2011/0287469 A1 | 11/2011 | Guenther |
| 2012/0003732 A1 | 1/2012 | Hung |
| 2012/0028818 A1 | 2/2012 | Ohman |
| 2012/0088693 A1 | 4/2012 | Lee |
| 2012/0135446 A1 | 5/2012 | Collins |
| 2012/0135452 A1 | 5/2012 | Shuler |
| 2012/0199487 A1 | 8/2012 | Stelzle |
| 2012/0214189 A1 | 8/2012 | Shuler |
| 2012/0318726 A1 | 12/2012 | Charest |
| 2012/0322097 A1 | 12/2012 | Charest |
| 2013/0059322 A1 | 3/2013 | Hung |
| 2013/0109594 A1 | 5/2013 | Gonda |
| 2013/0149735 A1 | 6/2013 | Prabhakarpandian |
| 2014/0038279 A1 | 2/2014 | Ingber |
| 2014/0158233 A1 | 6/2014 | Leslie |
| 2014/0186414 A1 | 7/2014 | Ingber |
| 2014/0199764 A1 | 7/2014 | Domansky |
| 2014/0248621 A1 | 9/2014 | Collins |
| 2014/0342445 A1 | 11/2014 | Ingber |
| 2015/0004077 A1 | 1/2015 | Wikswo |
| 2015/0079670 A1 | 3/2015 | Domansky |
| 2015/0209783 A1 | 7/2015 | Ingber |
| 2015/0306596 A1 | 10/2015 | Thompson |

FOREIGN PATENT DOCUMENTS

| | | |
|---|---|---|
| WO | WO 2015/006751 | 1/2015 |
| WO | WO 2015/013332 | 1/2015 |

(56) References Cited

FOREIGN PATENT DOCUMENTS

| WO | WO 2015/138032 | 9/2015 |
| WO | WO 2015/138034 | 9/2015 |

OTHER PUBLICATIONS

International Search Report for PCT/US2016/043674 dated Nov. 14, 2016 (5 pages).
Written Opinion of International Searching Authority for PCT/US2016/043674 dated Nov. 14, 2016 (12 pages).

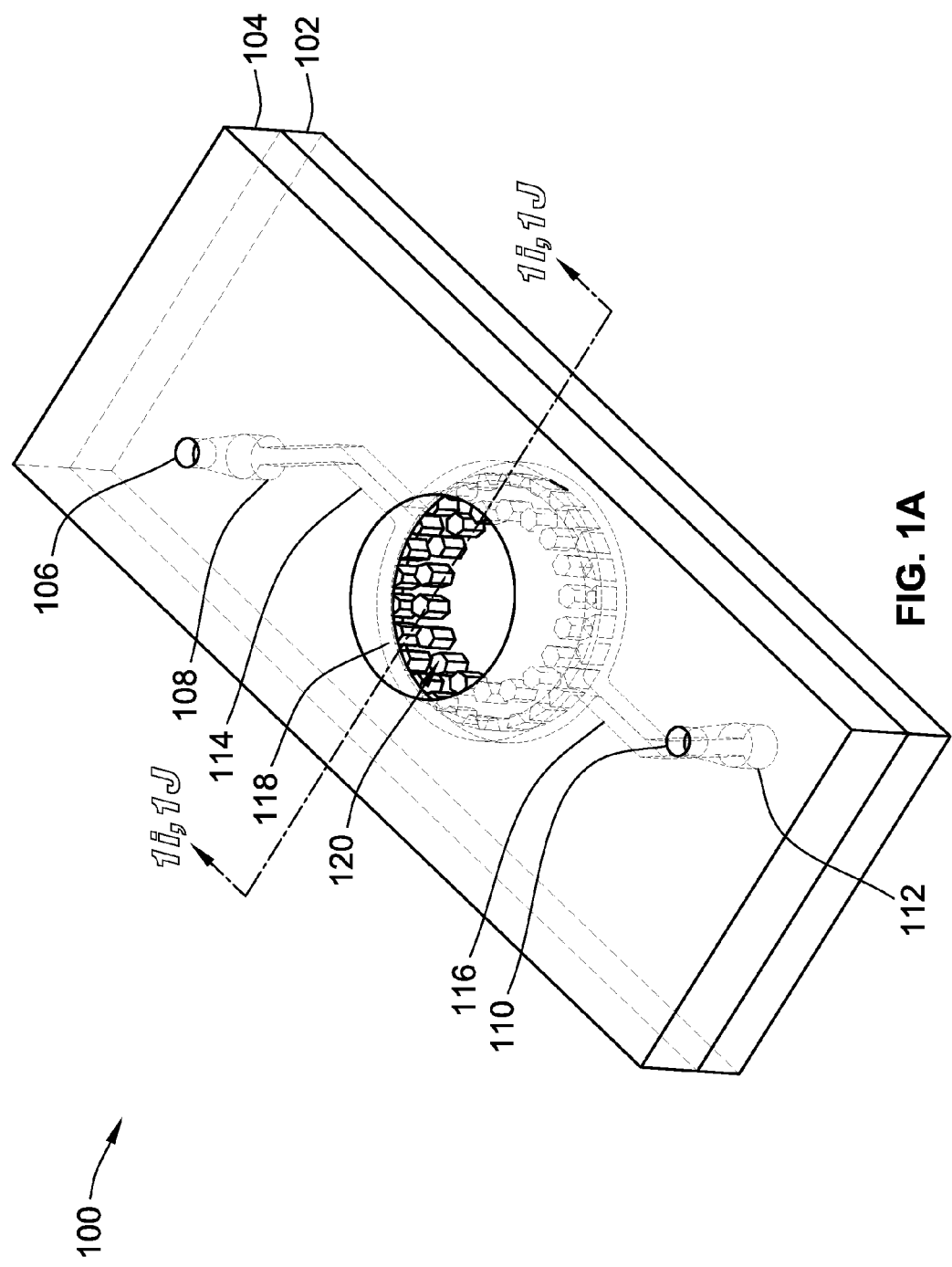

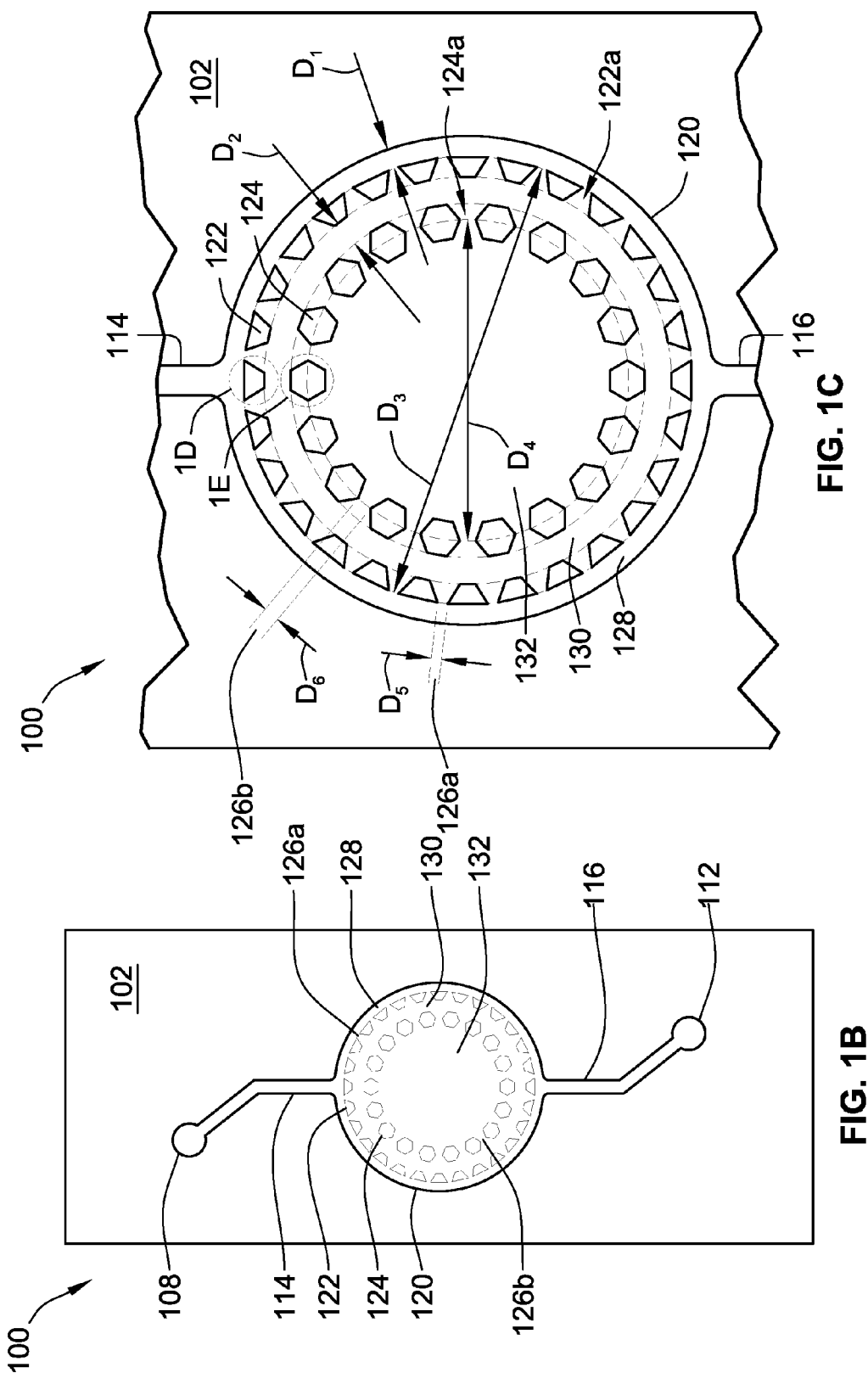

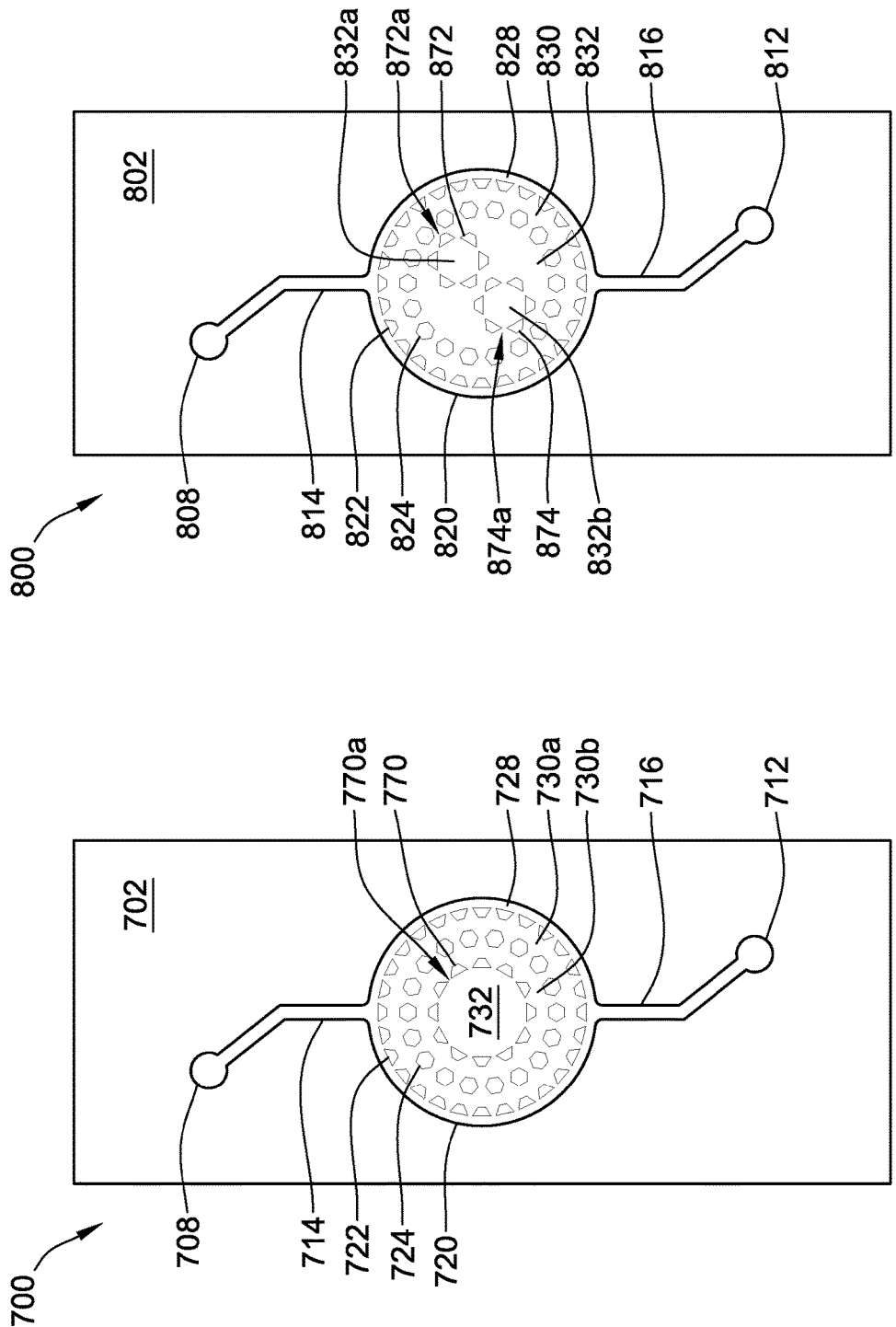

RADIAL MICROFLUIDIC DEVICES AND METHODS OF USE

CROSS-REFERENCE TO RELATED APPLICATION

The present application claims the benefit of and priority to U.S. Provisional Application No. 62/196,539, filed Jul. 24, 2015, and entitled, "MICROFLUIDIC RADIAL ORGAN CHIPS," the disclosure of which is hereby incorporated by reference herein in its entirety.

GOVERNMENT SUPPORT

This invention was made with government support under Contract No. HHSF223201310079C awarded by the U.S. Food & Drug Administration (FDA) and Contract No. W911NF-12-2-0036 awarded by the Department of Defense (DOD)/DARPA. The government has certain rights in the invention.

TECHNICAL FIELD

The present invention relates to cell culture systems and fluidic systems. More specifically, the present invention relates to devices, methods, and systems that allow for the forming of radial gradients within the cell culture systems and fluidic systems.

BACKGROUND

Microfluidic devices have been created that allow for the study of interactions within biological systems. More specifically, microfluidic devices exist that allow for the study of interactions between two channels, such as two fluid channels, separated by a membrane, such as a semi-permeable membrane. The membrane allows for cell migration, diffusion of soluble factors, etc. that are found in biological systems mimicked by the microfluidic devices. Such microfluidic devices have been created to study specific aspects of, for example, the human body, focusing on specific organs and/or tissues within the human body. These microfluidic devices are generally flat or planar, and the corresponding channel(s) and membrane(s) within these microfluidic devices also are generally flat or planar. The devices can be flat or planar because they are an approximation of small, flat organ sections, although the organ as a whole may be flat or curved. The generally flat or planar approximation of the microfluidic devices is possible because, for example, an intestine wall is effectively flat relative to a cell or soluble factor given the relative size difference; much like Earth is effectively flat relative to its inhabitants.

However, many biological systems can consist of concentric tissues or tubes, or tubes within tubes, that interact with one another through various mechanisms, including diffusion of soluble factors, cell migration, vascularization, and cell-to-cell contact at one or more interfaces. The concentric tissues or tubes found within biological systems consequently exhibit radial gradients of various components found within, such as radial gradients of cells or soluble factors. These radial gradients can be more important at smaller length scales. The conventional microfluidic devices that are generally flat or planar do not allow for the generation of these radial gradients, and also do not provide for radial interactions. The generally flat or planar microfluidic devices also may not allow for tissue formation, such as vascularization, between the two channels. The generally flat or planar microfluidic devices also may not easily accommodate more than two channels, or may not allow for the loading of fluid and/or material into the devices. These drawbacks limit or prevent the study of complex processes that normally occur between three or more tissue layers, such as the processes involved in bone marrow interactions with bone and vasculature, cancer cells with vascular and lymphatic endothelium, and the like.

Another possible drawback with conventional microfluidic devices that are generally flat or planar is that imaging of the processes within the devices must occur through the devices themselves, such as through top portions or bottom portions of the devices. In addition, or in the alternative, the generally flat or planar nature of the conventional microfluidic devices results in stacking of the two channels. The stacked channels result in imaging of one channel also capturing the other channel. In other words, the top and bottom channels are imaged at once, which inhibits or prevents detailed, real-time analysis of the interfacial processes from a tissue cross-section vantage point. For example, to observe the interface of tissues in conventional microfluidic devices, confocal microscopy can be used to look at the relationship of cells at the interface because of the optical overlap of top and bottom channels. However, confocal microscopy requires staining and the microfluidic devices being fixed, which prevents multiple time point analyses for the same microfluidic device.

Another possible drawback with conventional microfluidic devices that are generally flat or planar is that the devices are limited to having channels and not, for example, wells. The channels require a steady stream of fluid to pass into and out of the devices, rather than having fluid remain within the devices, such as in a batch process within a well. Thus, batch process sampling within the device is not possible.

The below-described devices, methods, and systems solve many of the problems associated with the current art by providing concentric (or eccentric) channels, rings, and wells within a microfluidic device that allow for the generation and analysis of radial gradients. The below-described devices, methods, and systems also provide access to one or more of the channels, rings, and wells for imaging the processes within the devices, specific to the channels, rings, and wells, or interfaces therebetween. The open design of the devices and systems also provide for simultaneous sampling of one or more of the channels, rings, and wells for further analysis of the processes occurring therein.

SUMMARY

According to aspects of the present disclosure, radial microfluidic devices are presented that provide for the generation of radial gradients between one or more channels, rings, and/or wells to mimic the processes that are found in concentric tissues and tubes (or tubes within tubes) within biological systems. The one or more channels allow for the continuous flow of fluid and material around the perimeters of one or more rings and/or wells, which can contain fluid and/or material therein, to generate the radial gradients within the one or more rings and/or wells.

According to additional aspects of the present disclosure, radial microfluidic devices are presented that provide for the generation of radial gradients to mimic one or more biological systems. The radial microfluidic devices include removable lids and/or lids with openings therein to provide for direct access to one or more channels, rings, and/or wells within the devices. The removable lids and/or openings allow for the direct sampling and/or imaging of the one or more channels, rings, and/or wells, or the interfaces therebetween.

According to further aspects of the present disclosure, radial microfluidic devices are presented that allow for tissue formation between one or more channels, rings, and/or wells. The tissue formation can occur between a channel and a well, separated by a ring containing a semi-permeable membrane to mimic, for example, vascularization or similar processes that occur in biological systems.

According to still additional aspects of the present disclosure, radial microfluidic devices are presented that include chambers. Within the chambers are arrays or rings of posts that define one or more chamber channels, chamber rings, and/or chamber wells. Based at least in part on the geometries of the posts, the posts can constrain fluids with the chamber to the one or more chamber channels, chamber rings, and/or chamber wells. The resulting distribution of the fluid replicates one or more biological systems having concentric tissue or tubes (tubes within tubes).

According to additional aspects of the present disclosure, a microfluidic device is disclosed. The device includes an inlet channel configured to flow fluid into the device, and an outlet channel configured to flow the fluid out of the device. The device further includes a chamber having an open top. The chamber is in fluid communication with the inlet channel and the outlet channel to flow fluid through the chamber. The device also includes a plurality of outer posts and a plurality of inner posts. Each outer post is spaced apart from adjacent outer posts and arranged to define an outer post ring. Each inner post is spaced apart from adjacent inner posts and arranged to define an inner post ring. The device is further configured so that a wall of the chamber and the outer post ring define a chamber channel within the chamber. The device is further configured so that the outer post ring and the inner post ring define a chamber ring within the chamber. Further, the device is configured so that the inner post ring defines a chamber well within the chamber.

According to further aspects of the present disclosure, a method of preparing a microfluidic device for simulating a function or response of a tissue is disclosed. The method includes loading one or more chamber wells of a microfluidic device with one or more fluids. When loaded within the one or more chamber wells, the one or more fluids are confined within the one or more chamber wells by one or more rings of inner posts. After loading, the one or more fluids in the one or more chamber wells are allowed to set. The method further includes loading one or more chamber rings of the microfluidic device with one or more fluids. When loaded within the one or more chamber rings, the one or more fluids are confined within the one or more chamber rings by one or more rings of outer posts and the one or more rings of inner posts. After loading, the one or more fluids in the one or more chamber rings are allowed to set.

In some additional aspects of the above method, fluid is flowed through one or more chamber channels within the microfluidic device. The one or more chamber channels are adjacent to and surround at least one of the one or more chamber rings, the one or more chamber wells, or a combination thereof. Further, the flowing of the fluid through the one or more chamber channels at steady-state causes one or more gradients within the one or more chamber wells. Variations in one or more cell concentrations, one or more factor concentrations, and the like can form the gradients within the one or more chamber wells.

According to still additional aspects of the present disclosure, a microfluidic device is disclosed. The device includes a chamber well within a base. In particular, the chamber well includes an open top. The device further includes a semi-permeable membrane surrounding and co-planar with the chamber well. The device also includes a chamber channel surrounding and co-planar with the semi-permeable membrane. The device has an inlet channel within the base that is in fluid communication with the chamber channel, in addition to an outlet channel within the base that is in fluid communication with the chamber channel and the inlet channel. The device, as configured, allows for fluid to flow into the chamber channel and around the semi-permeable membrane from the inlet channel, and out of the chamber channel through the outlet channel.

According to further aspects, a microfluidic device for simulating a function or response of a tissue is disclosed. The device includes an inlet for receiving a fluid in the device and an outlet for removing the fluid from the device. The device further includes a pair of distinct fluid channels leading from the inlet to the outlet for flowing the fluid through the device. The pair of fluid channels is spatially separated so as to define a chamber well between the pair of fluid channels, and the chamber well receives cells associated with the tissue. The device also includes an interface structure between at least one of the fluid channels and the chamber well for permitting migration of at least one of cells, particulates, chemicals, molecules, liquids, or gases between the fluid within the at least one of the fluid channels and the chamber well.

According to additional aspects, a microfluidic device for simulating a function or response of a tissue is disclosed. The device includes a base layer having a chamber well receiving cells associated with the tissue, a lid layer in contact with the base layer, and a pair of distinct fluid channels defined by the base layer and the lid layer. The pair of fluid channels is spatially separated by the chamber well. The device also includes an interface structure between at least one of the fluid channels and the chamber well for permitting migration of at least one of cells, particulates, chemicals, molecules, liquids, or gases between the fluid and the cells within the chamber well.

According to yet additional aspects, a microfluidic device for simulating a function or response of a tissue is disclosed. The device includes a base layer having a chamber well receiving cells associated with the tissue. The chamber well has a periphery that includes a curved portion. The device also includes a lid layer in contact with the base layer. The device further includes a fluid channel defined by the base layer and the lid layer for flowing the fluid through the device. The fluid channel extends along at least the curved portion of the periphery of the chamber well. The device includes an interface structure between the fluid channel and the chamber well for permitting migration of at least one of cells, particulates, chemicals, molecules, liquids, or gases between the fluid and the cells within the chamber well.

According to further aspects, a microfluidic device for simulating a function or response of a tissue is disclosed. The device includes a chamber well having a periphery that includes a curved portion, and a fluid channel extending along at least the curved portion. The device further includes an interface structure between the fluid channel and the chamber well for permitting migration of at least one of cells, particulates, chemicals, molecules, liquids, or gases between the fluid and the cells within the chamber well.

According to some additional aspects, a method of simulating a function or response of a tissue is disclosed. The method includes flowing fluid into a microfluidic device, the fluid containing one or more components associated with the tissue. The method further includes flowing the fluid around a chamber well within the microfluidic device. In some aspects, the chamber well contains one or more components associated with the tissue. Further, the fluid is separated from the chamber well by an interface structure permitting migration of the one or more fluid components, the one or more chamber well components, or a combination thereof between the fluid and the chamber well. The method further includes flowing the fluid out of the device.

According to yet additional aspects, a microfluidic device is disclosed that includes a chamber. The chamber is defined by one or more walls and includes a lumen. The lumen includes one or more geometric features. The microfluidic device further includes a gel confined by the one or more geometric features. The gel includes cells and the cells are in contact with fluid from one or more fluidic channels. In one embodiment, said fluidic channels are microchannels.

According to further aspects, a method of culturing cells is disclosed. The method includes providing microfluidic device comprising a chamber. The chamber includes geometric features and a lumen. The lumen is covered by a removable lid and is in fluidic communication with one or more fluidic channels. In one embodiment, said fluidic channels are microchannels. The chamber further includes a material capable of forming a gel and cells. The method further includes removing the removable lid, and introducing the material under conditions such that a gel forms in the lumen, in which the gel is confined by one or more of said geometric features. The method further includes introducing the cells to the gel, with the cells being in contact with fluid from said one or more fluidic channels.

According to additional aspects, a method of detecting cell migration is disclosed. The method includes providing a microfluidic device. The microfluidic device includes a chamber that is defined by one or more walls and includes a lumen. The lumen includes a flow channel that is defined by one or more geometric features. The microfluidic device further includes a first gel that includes first cells, is confined by the one or more geometric features, and is surrounded by the flow channel. The first cells are contact with fluid from one or more fluidic channels. In one embodiment, said fluidic channels are microchannels. The microfluidic device further includes a second gel in the flow channel that includes second cells. The method further includes detecting migration of the first cells toward the second cells.

These and other capabilities of the inventions, along with the inventions themselves, will be more fully understood after a review of the following figures, detailed description, and claims.

Definitions

The term "microfluidic" as used herein relates to components where moving fluid is constrained in or directed through one or more channels wherein one or more dimensions are 1 mm or smaller (microscale). Microfluidic channels may be larger than microscale in one or more directions, though the channel(s) will be on the microscale in at least one direction. In some instances, the geometry of a microfluidic channel may be configured to control the fluid flow rate through the channel (e.g., increase channel height to reduce shear). Microfluidic channels can be formed of various geometries to facilitate a wide range of flow rates through the channels.

The term "channels" as used herein relates to pathways (whether straight, curved, single, multiple, in a network, etc.) through a medium (e.g., silicon) that allow for movement of liquids and gasses. Channels thus can connect other components, i.e., keep components "in communication" and more particularly, "in fluidic communication" and still more particularly, "in liquid communication." Such components include, but are not limited to, liquid-intake ports and gas vents. Microchannels are channels with dimensions less than 1 millimeter and greater than 1 micron.

As used herein, the phrases "connected to," "coupled to," "in contact with," and "in communication with" refer to any form of interaction between two or more entities, including mechanical, electrical, magnetic, electromagnetic, fluidic, and thermal interaction. For example, in one embodiment, channels in a microfluidic device are in fluidic communication with cells and (optionally) a fluid reservoir. Two components may be coupled to each other even though they are not in direct contact with each other. For example, two components may be coupled to each other through an intermediate component (e.g., tubing or other conduit).

Other than in the operating examples, or where otherwise indicated, all numbers expressing quantities of ingredients or reaction conditions used herein should be understood as modified in all instances by the term "about." The term "about" when used to described the present invention in connection with percentages means±5%.

As used herein, the term "substantially" means a proportion of at least about 60%, or preferably at least about 70%, or at least about 80%, or at least about 90%, or at least about 95%, or at least about 97%, or at least about 99% or more, or any integer between 70% and 100%. In some embodiments, the term "substantially" means a proportion of at least about 90%, at least about 95%, at least about 98%, at least about 99% or more, or any integer between 90% and 100%. In some embodiments, the term "substantially" can include 100%.

BRIEF DESCRIPTION OF THE DRAWINGS

While the inventions are susceptible to various modifications and alternative forms, specific embodiments have been shown by way of example in the drawings and will be described in detail herein. It should be understood, however, that the inventions are not intended to be limited to the particular forms disclosed. Rather, the inventions are to cover all modifications, equivalents, and alternatives falling within the spirit and scope of the inventions as defined by the appended claims.

FIG. 1A illustrates a perspective view of a radial microfluidic device, in accord with some aspects of the present concepts.

FIG. 1B illustrates a top view of the radial microfluidic device of FIG. 1A, with a lid removed, in accord with some aspects of the present concepts.

FIG. 1C illustrates a detailed top view of a chamber of the radial microfluidic device of FIG. 1A, in accord with some aspects of the present concepts.

FIG. 7 illustrates a top view of another alternative radial microfluidic device, with a lid removed, in accord with some aspects of the present concepts.

FIG. 8 illustrates a top view of another alternative radial microfluidic device, with a lid removed, in accord with some aspects of the present concepts.

DETAILED DESCRIPTION

Figure 1D:
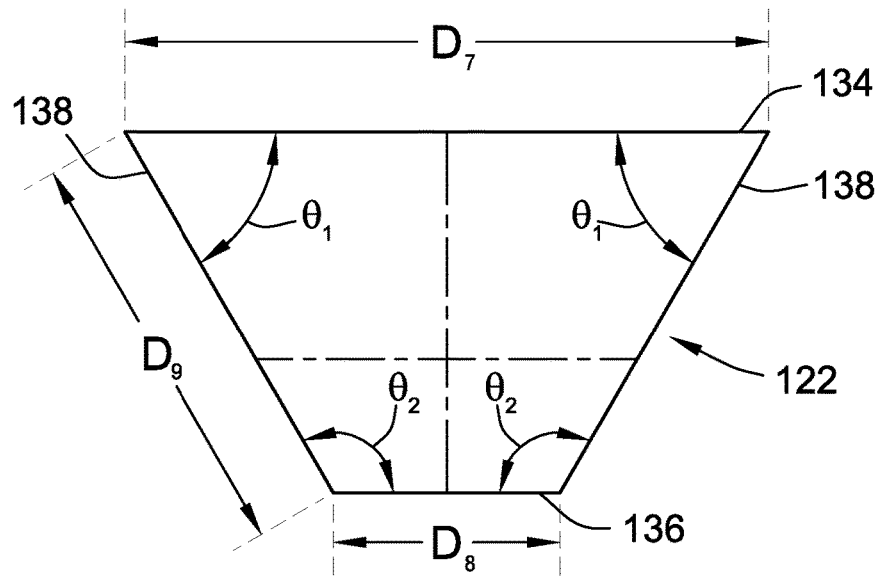
FIG. 1D illustrates a plan view of a post within the radial microfluidic device of FIG. 1A, in accord with some aspects of the present concepts.

While the inventions are susceptible of embodiment in many different forms, there is shown in the drawings and will herein be described in detail preferred embodiments of the inventions with the understanding that the present disclosure is to be considered as an exemplification of the principles of the inventions and is not intended to limit the broad aspects of the inventions to the embodiments illustrated.

The functionality of cells and tissue types (and even organs) can be implemented in one or more microfluidic devices or "chips" that enable researchers to study these cells and tissue types outside of the body while mimicking much of the stimuli and environment that the tissue is exposed to in vivo. It can also be desirable to implement these microfluidic devices into interconnected components that can simulate groups of organs or tissue systems. Preferably, the microfluidic devices can be easily inserted and removed from an underlying fluidic system that connects to these devices in order to vary the simulated in vivo conditions and organ systems.

FIG. 1A illustrates a perspective view of microfluidic device, specifically a radial microfluidic device 100, which is one type of an organ-on-chop ("OOC") device, in accord with some aspects of the present concepts. The device 100 includes a base 102 and a lid 104 above the base 102. The base 102 is preferably made of a transparent polymeric material, such as polydimethylsiloxane (PDMS). However, the base 102 can be made of other transparent or opaque materials, such as other polymeric materials and/or other non-polymeric materials, including thermoplastics, thermoset polymers, biodegradable material(s), glasses, metals, ceramics, hydrogels, biopolymers, and the like. In some aspects, the base 102 can be formed of a biodegradable material. In some aspects, the biodegradable material can be designed to degrade within a body, such as a human body. In which case, the device 100 can be inserted into a human body. The device 100 can be inserted into the human body for various purposes, such as to perform one or more tests using the device 100, seed one or more cells within the human body for tissue engineering and/or regenerative medicine, such as seed one or more bone cells within a bone. In some aspects, the device 100 can be implanted with the human body (or any other animal body) for in vivo testing of various applications. Implantation can occur after tissue maturation within the device 100, or prior to tissue maturation. After a designed period of time, the device 100 can degrade. Such biodegradable materials include, for example, polycaprolactone, poly lactic-co-glycolic acid, gelatin, collagen, chitosan, and the like.

The lid 104 sits above the base 102 and seals the base 102. In particular, and in the case of open channels in the base 102, the lid 104 seals the open channels to prevent or inhibit fluid from escaping the open channels and/or the base 102. The lid 104 is preferably made of a transparent polymeric material, such as PDMS, but can be made of other transparent or opaque materials, such as other polymeric materials and/or other non-polymeric materials, including the materials listed above for the base 102. In some aspects, the lid 104 is made of a translucent material to aid in visualizing or imaging the biological processes occurring within the device 100.

In some aspects, the lid 104 can be removable from the base 102. For example, the lid 104 can be placed on the base 102 without any mechanical coupling and/or chemical adhesion with the base 102. In such a case, the lid 104 can still provide a seal with the base 102 to prevent fluids from escaping from the base 102 and/or open channels within the base 102. Alternatively, the lid 104 can be placed on the base 102 and mechanically and/or chemically coupled to the base 102 such that, with minimal force, the lid 104 can be removed from the base 102. In alternative aspects, the lid 104 can be fixed to the base 102 so as to be not removable from the base 102 under normal forces and/or loads. In such a case, the lid 104 can be mechanically coupled and/or chemically adhered to the base 102 so as to be not removable. In some aspects, the lid 104 can be a sealing film, rather than a rigid body.

Within the lid 104 is formed an inlet port 106 that is in fluid communication with a fluid inlet 108 within the base 102. The inlet port 106 and the fluid inlet 108 also are in fluid communication with an inlet channel 114 in the base 102. Similarly, within the lid 104 is an outlet port 110 that is in fluid communication with a fluid outlet 112 within the base 102. The outlet port 110 and the fluid outlet 112 also are in fluid communication with an outlet channel 116 in the base 102. Although shown as being formed within the top surface of the lid 104, alternatively, the inlet port 106 and the outlet port 110 can be formed in one or two of the side surfaces of the lid 104, surrounding the top surface. Further, although the terms inlet and outlet are used herein, the terms are not meant to be limiting and are instead merely used for convenience of describing the device 100 and the flow of fluid therein. For example, in some aspects, the inlet port 106, the fluid inlet 108, and the inlet channel 114 can instead be used to flow fluid and/or solids out of the device 100, and the outlet port 110, the fluid outlet 112, and the outlet channel 116 can instead be used to flow fluid and/or solids into the device 100. Further, the term fluid as used herein is meant to cover one or more fluids, and, optionally, one or more dissolved and/or suspended solids (e.g., cells, particulates, chemicals, molecules, liquids, gases, factors, such as but not limited to vascular endothelial growth factors (VEGFs), erythropoietin, cytokines, other growth factors, hormones, pro- or anti-inflammatory molecules, and other factors, nutrients, cell media, etc.) contained therein, unless explicitly used to the contrary or disclaimed. Thus, the inlet port 106, the fluid inlet 108, and the inlet channel 114, as well as the outlet port 110, the fluid outlet 112, and the outlet channel 116, can generally be used to flow fluid into, through, and out of the device 100.

The inlet port 106 is generally configured to connect to a fluid line (not shown) to provide fluid to the device 100. For example, a fluid line can be inserted into the inlet port 106. Alternatively, the fluid line can attach to the top surface of the lid 104 around the inlet port 106. Similarly, the outlet port 110 is generally configured to connect to a fluid line (not shown) to withdraw or remove the fluid from to the device 100. The fluid lines can be part of a larger fluidic system that connects the device 100 to other microfluidic devices (including other devices 100) in order to vary the simulated in vivo conditions and organ systems, or to generate a larger fluid system.

In some aspects, the base 102 and the lid 104, including the various features discussed below, can be formed using injection molding and/or hot embossed using thermoplastics, or cast using thermoset polymers. In some aspects, the features of the base 102 and/or lid 104 can be formed using lithography.

The base 102 includes a chamber 120. As illustrated, the chamber 120 is generally a circular recess within the base 102. However, the chamber 120 can be various shapes other than circular, such as triangular, rectangular, square, oval, pentagonal, hexagonal, heptagonal, etc., including non-uniform and/or non-symmetric shapes. The chamber 120 is positioned such that the plane of the circumference of the chamber 120 is generally within the plane of the base 102. Further, the wall of the chamber 120 is generally orthogonal to the top and bottom surfaces of the base 102. However, the walls of the chamber 120 can be oblique to the top and bottom surfaces of the base 102 without departing from the scope of the present disclosure.

The lid 104 further includes an opening 118 that is aligned with the chamber 120 with the lid 104 seated on the base 102. In some aspects, the lid 104 includes the opening 118 regardless of whether the lid 104 is removable from the base 102. In the case of the lid 104 being fixed to the base 102, the opening 118 provides access to the interior of the chamber 120 with the lid 104 seated on the base 102.

The chamber 120 is in fluid communication with the inlet port 106, the fluid inlet 108, and the inlet channel 114, as well as the outlet port 110, the fluid outlet 112, and the outlet channel 116. In some aspects, the chamber 120 can be considered a recess that is formed within the base 102, such as by removing material from the base 102 to from the chamber 120. In alternative aspects, the chamber 120 can be formed at the time of forming the base 102, such as by, for example, injection molding where the molding includes an inverse element corresponding to the chamber 120. According to any method of forming the chamber 120, the chamber 120 is formed with an open top so as to provide access to the interior of the chamber 120 from the exterior of the base 102. Further, with the opening 118 in the lid 104, or by having a removable lid 104, without or without the opening 118, the chamber 120 can also be accessed from the exterior of the device 100.

As illustrated, the inlet channel 114 can be opposite from the outlet channel 116 relative to the chamber 120. Fluid flow from the inlet channel 114 enters the chamber 120 and flows uniformly across the chamber to the outlet channel 116. However, in some aspects, the inlet channel 114 and/or the outlet channel 116 can interface with (e.g., connect to) the chamber 120 in other locations and other positions relative to each other. For example, rather than the current 180° arrangement of the inlet channel 114 relative to the outlet channel 116 illustrated in FIG. 1B, the outlet channel 116 can be positioned at 90°, 120°, 270°, etc. around the chamber 120 relative to the inlet channel 114.

Referring to FIG. 1B, the chamber 120 includes a plurality of posts. More specifically, the chamber 120 includes a plurality of posts 122. The posts 122 extend up from the bottom of the chamber 120. The posts 122 can be formed of the same material as the base 102 listed above. Where the posts 122 are formed of the same material as the base 102, the posts 122 and the base 102 can be formed using a single fabrication process, such as by injection molding or lithography. With respect to lithography, as an example, a solid blank can be used to form the base 102, and where the blank is etched to form the various features within the base 102, such as the chamber 120, the posts 122, and the various features of the fluid pathways (e.g., the inlet port 106, the fluid inlet 108, and the inlet channel 114, as well as the outlet port 110, the fluid outlet 112, and the outlet channel 116). In alternative aspects, the posts 122 can be formed of different materials than the base 102. In some aspects, the posts 122 can be formed of a material that can later be dissolved away, such as after forming other features within the chamber 120, as further described below. The posts 122 can be dissolved based on flowing one or more specific fluids within the chamber 120 that are designed to dissolve the posts 122. In some aspects, the posts 122 can be formed of a biodegradable, thermally degradable, or chemically degradable material that can be degraded by fluid within the chamber 120. In some aspects, the biodegradable material can be designed to degrade within a body, such as a human body, as described above with respect to the base 102. Posts could be made of degradable materials such as polymers containing peptide or ester bonds that can be degraded by naturally occurring enzymes, thermally-degradable polymers such as gelatin, or chemically degradable compounds that can, for example, contain disulfide bonds or multivalent ionic bonds that can be dissolved with chelators or other chemicals.

As shown, the posts 122 are arranged within the chamber 120 such that there are gaps 126a between adjacent posts 122, and the posts 122, as a whole, form an array or a ring 122a (FIG. 1C). The ring 122a can be circular, as shown, and can be concentric with the chamber 120. Alternatively, the ring 122a can be eccentric with the chamber 120. Further, although shown as being generally circular, the ring 122a can form other shapes, such as triangular, rectangular, square, oval, pentagonal, hexagonal, heptagonal, etc., including non-uniform and/or non-symmetric shapes. Between the ring 122a and the wall of the chamber 120 forms a chamber channel 128. The chamber channel 128 is in fluid communication with the inlet port 106, the fluid inlet 108, and the inlet channel 114, as well as the outlet port 110, the fluid outlet 112, and the outlet channel 116, and surrounds the ring 122a of posts 122. The chamber channel 128 can be considered a single channel that surrounds the ring 122a of posts 122, such as a single circular channel that neither starts nor ends. However, additionally, the chamber channel 128 can be considered a pair of channels, such as a right channel along the right side of the ring 122a of posts 122, and a left channel along the left side of the ring 122a of posts 122. The right and left channels each start at the inlet channel 114 and end at the outlet channel 116. In both cases, fluid can flow from the inlet channel 114, to within the chamber channel 128 around the ring 122a of posts 122, as discussed below, and out of the outlet channel 116.

The chamber 120 further includes a plurality of posts 124. The posts 124 extend up from the bottom of the chamber 120. The posts 124 are arranged within the chamber 120 to define an array or a ring 124a (FIG. 1C). The posts 124 can be formed of the same or different materials as the base 102 and/or the posts 122 listed above. Where the posts 124 are formed of the same material used to form the base 102, or the base 102 and the posts 124, the base 102 and the posts 122 and 124 can be formed using a single fabrication process, as described above. In alternative aspects, the posts 124 can be formed of different materials than the base 102 and/or the posts 122. Like the posts 122, the posts 124 also can be formed of a material that can later be dissolved away. The posts 124 can be dissolved based on flowing one or more specific fluids within the chamber 120 that are designed to dissolve the posts 124. In some aspects, the posts 124 can be formed of a biodegradable material that can be degraded by fluid within the chamber 120. In some aspects, the biodegradable material can be designed to degrade within a body, such as a human body, as described above with respect to the base 102 and the posts 122.

As shown, the posts 124 are arranged within the chamber 120 such that there are gaps 126b between adjacent posts 124, and the posts 124, as a whole, form a ring 124a (FIG. 1C). The ring 124a can be circular, as shown, and can be concentric with the chamber 120 and/or the ring 122a. Alternatively, the ring 124a can be eccentric with either one or both of the chamber 120 and the ring 122a. Further, although shown as being generally circular, the ring 124a can form other shapes, such as triangular, rectangular, square, oval, pentagonal, hexagonal, heptagonal, etc., including non-uniform and/or non-symmetric shapes. Between the ring 124a and the ring 122a forms a chamber ring 130. Additionally, within the ring 124a forms a chamber well 132. Although appearing to be in fluid communication with the inlet port 106, the fluid inlet 108, and/or the inlet channel 114, as well as the outlet port 110, the fluid outlet 112, and the outlet channel 116, for reasons discussed in greater detail below, the chamber ring 130 and the chamber well 132 can be substantially not in fluid communication with the foregoing inlet and outlet features during use.

FIG. 1C illustrates a detailed top view of the chamber 120 of the device 100, in accord with some aspects of the present concepts. More specifically, FIG. 1C shows the various distances between the features of the chamber 120. Beginning with the width of the chamber channel 128—also described as the distance $D_1$ between the outer edges of the posts 122, defining the ring 122a, and the wall of the chamber 120—the width can be, for example, about 0.4 millimeter (mm) to about 0.6 mm, such as about 0.5 mm. The width of the chamber ring 130—also described as the distance $D_2$ between the inner edges of the posts 122, defining the ring 122a, and the outer edges of the posts 124, defining the ring 124a—can be, for example, about 0.5 mm to about 1.0 mm, such as about 1.0 mm. The outer diameter of the ring 122a—also described as the distance $D_3$ between opposite outer edges of the ring 122a—can be, for example, about 9 mm to about 10 mm, such as about 10 mm. The diameter of the ring 124a—also described as the distance $D_4$ between centers of opposite posts 124—can be, for example, about 6.0 mm to about 7.0 mm, such as about 6.5 mm. The spacing between posts 122—also described as the distance $D_5$—can be, for example, about 0.20 mm to about 0.40 mm, such as about 0.25 mm. The spacing between posts 124—also described as the distance $D_6$—can be, for example, about 0.25 mm to about 0.35 mm, such as about 0.29 mm. For reasons discussed in further detail below, the height of the posts 122 can be about the same height (or depth) as the chamber 120. For example, the height of the posts 122 can be about 1 mm to about 2 mm, such as about 2 mm. For reasons also discussed in further detail below, the height of the posts 124 can be about the same height as the posts 122, or shorter. For example, the height of the posts 124 can be about 1 mm to about 2 mm, such as about 2 mm. Although specific dimensions and/or ranges of dimensions are provided herein, the dimensions and/or ranges of dimensions are not meant to be limiting. Also, the dimensions and/or ranges of dimensions can vary, as further described below.

FIG. 1D illustrates a plan view of the posts 122 within the device 100, in accord with some aspects of the present concepts. In one aspect, and as shown, the posts 122 have a trapezoidal shape. However, the posts 122 can have various other shapes that conform to the description below with respect to the exterior angles, such as pentagons, hexagons, circles, ovals, rounded geometries, triangles, etc. With respect to trapezoids, in particular, it has been found that the shape of a trapezoid provides better contact angles for surface tension of fluids (e.g., liquids, gels, etc.) to constrain the fluids by the posts 122, for the reasons described below. Based on the trapezoidal shape, the outer edge 134 is longer than the inner edge 136. Further, the side edges 138 are the same length.

According to the dimensions and ranges of dimensions provided above, the length of the outer edge 134—also described as the distance $D_7$—can be, for example, about 0.80 mm to about 0.90 mm, such as about 0.85 mm. The length of the inner edge 136—also described as the distance $D_8$—can be, for example, about 0.25 mm to about 0.35 mm, such as about 0.30 mm. The length of the side edges 138—also described as the distance $D_9$—can be, for example, about 0.50 mm to about 0.60 mm, such as about 0.55 mm. For these distances, the angle $\theta_1$ between the outer edge 134 and the side edges 138 can be, for example, about 10° to about 170°, such as about 60°. Further, the angle $\theta_2$ between the inner edge 136 and the side edges 138 can be, for example, about 10° to about 170°, such as about 120°.

Figure 1E:
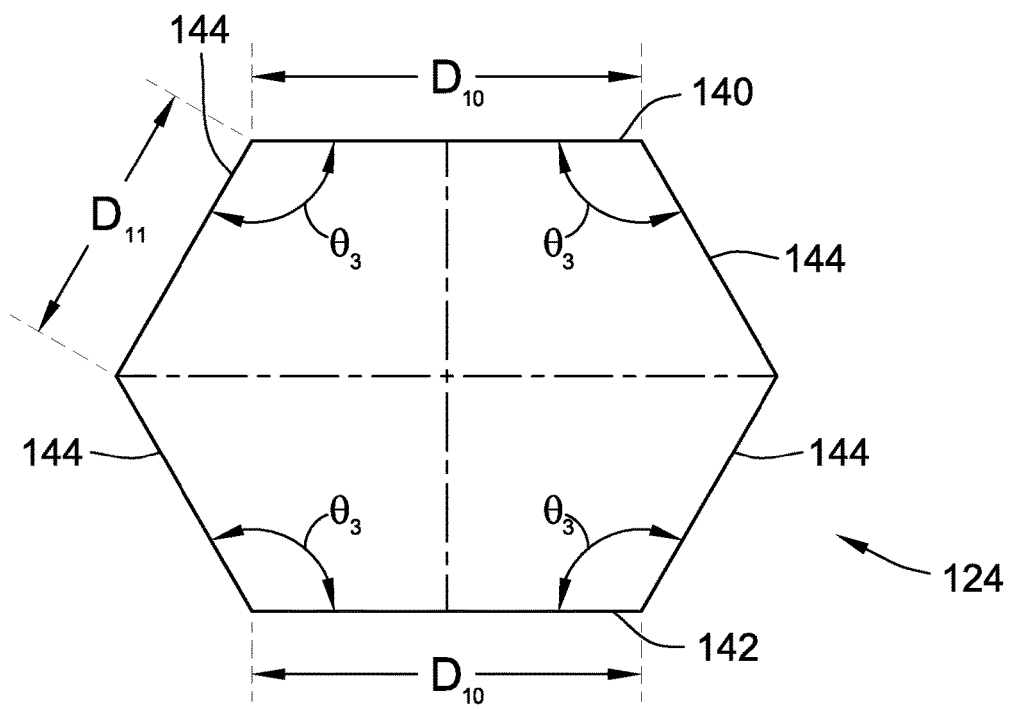
FIG. 1E illustrates a plan view of another post within the radial microfluidic device of FIG. 1A, in accord with some aspects of the present concepts.

FIG. 1E illustrates a plan view of the posts 124 within the device 100, in accord with some aspects of the present concepts. In one aspect, and as shown, the posts 124 have a hexagonal shape. However, the posts 124 can have various other shapes that conform to the description below with respect to the exterior angles, and the interaction of the shapes with the fluids. The alternative shapes include the shapes discussed above with respect to the posts 122, including the posts 124 being the same shape as the posts 122 or different shapes as the posts 122, as illustrated. Like trapezoids, it has been found that the shape of a hexagon provides better contact angles for surface tension of fluids (e.g., liquids, gels, etc.) to constrain the fluids by the posts 124, for the reasons described below. Based on the hexagonal shape, the outer edge 140 is about the same length as the inner edge 142. Further, the side edges 144 are the same length. According to the dimensions and ranges of dimensions provided above, the lengths of the outer edge 140 and the inner edge 142—also described as the distance $D_{10}$—can be, for example, about 0.45 mm to about 0.55 mm, such as about 0.50 mm. The length of the side edges 144—also described as the distance $D_{11}$—can be, for example, about 0.30 mm to about 0.40 mm, such as about 0.35 mm. For these distances, the angle $\theta_3$ between the outer edge 140, or the inner edge 142, and the side edges 144 can be, for example, about 10° to about 170°, such as about 120°.

Figure 1F:
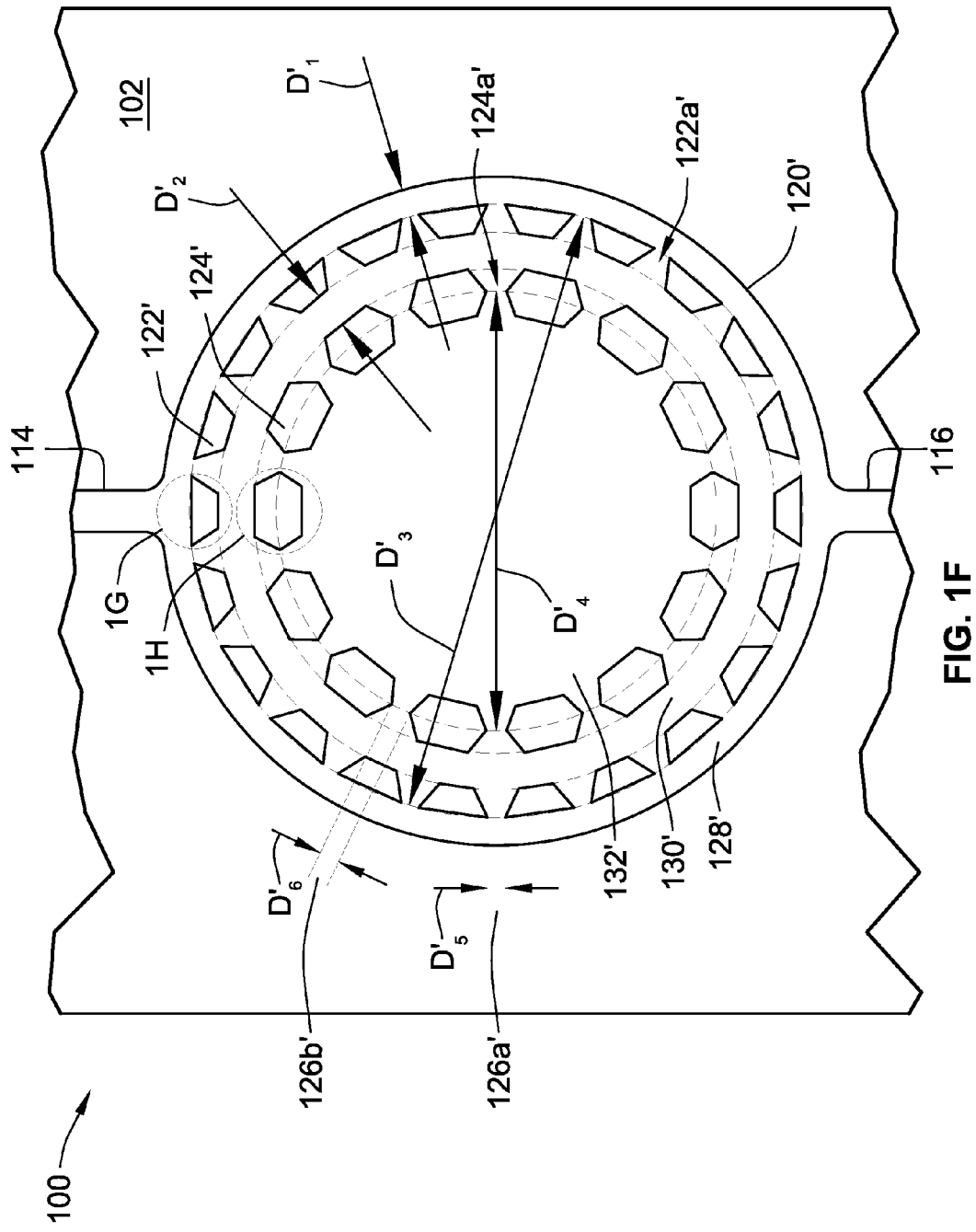
FIG. 1F illustrates a detailed top view of an alternative chamber of the radial microfluidic device of FIG. 1A, in accord with some aspects of the present concepts.

FIG. 1F illustrates a detailed top view of an alternative chamber 120' of the device 100, in accord with some aspects of the present concepts. The chamber 120' is described as an alternative chamber 120' based on having different geometries and arrangements of the posts 122' and 124', relative to the posts 122 and 124 of the chamber 120. In some aspects, the geometries and dimensions of the posts 122' and 124' illustrated and described with respect to FIGS. 1F-1H, in addition to the gaps between the posts 122' and 124', allow for more robust fabrication of the device 100, and particularly of the base 102. For example, larger posts 122' and 124', as compared to posts 122 and 124, may not cause molds used to form the base 102 during fabrication, such as during a soft lithography peeling process, to tear. Further, the larger posts 122' and 124' can reduce the need for degassing steps prior to the molding.

Beginning with the width of the chamber channel 128'—also described as the distance $D_1'$ between the outer edges of the posts 122', defining the ring 122a', and the wall of the chamber 120'—the width can be, for example, about 0.5. The width of the chamber ring 130'—also described as the distance $D_2'$ between the inner edges of the posts 122', defining the ring 122a', and the outer edges of the posts 124', defining the ring 124a'—can be, for example, about 1.0 mm. The outer diameter of the ring 122a'—also described as the distance $D_3'$ between opposite outer edges of the ring 122a'—can be, for example, about 10 mm. The diameter of the ring 124a'—also described as the distance $D_4'$ between centers of opposite posts 124'—can be, for example, about 6.5 mm. This size of the ring 124' aids in loading fluid within the chamber ring 130. For example, too small of a ring 124' may inhibit pipetting fluid within the chamber ring 130, although pipetting at small dimensions, such as 5 mm, can be feasible. The spacing between posts 122'—also described as the distance $D_5'$—can be, for example, about 0.34 mm. The spacing between posts 124'—also described as the distance $D_6'$—can be, for example, about 0.29 mm. The height of the posts 122' can be about 1 mm. This can be shorter than the height of the walls of the chamber 120'. The height of the posts 124' can be about the same height as the posts 122'.

Figure 1G:
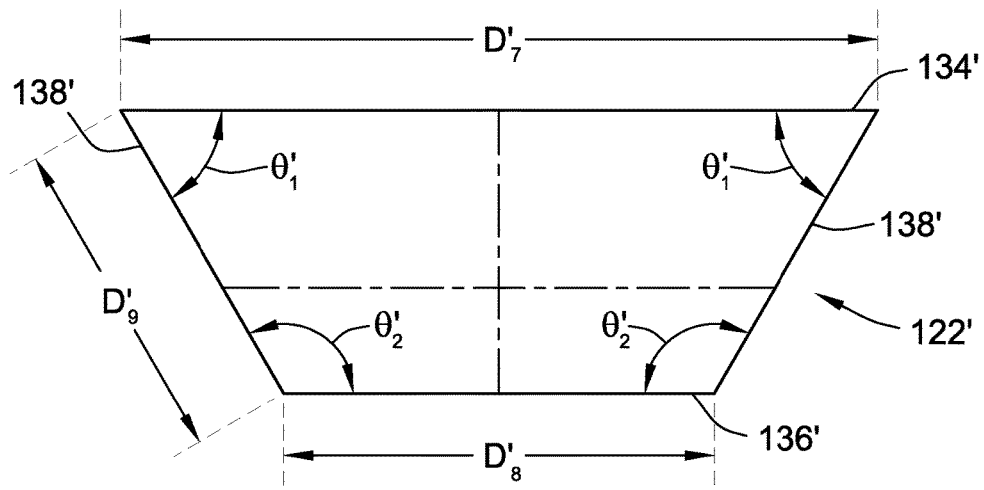
FIG. 1G illustrates a plan view of a post within the alternative chamber of FIG. 1F, in accord with some aspects of the present concepts.

FIG. 1G illustrates a plan view of the posts 122' within the device 100, in accord with some aspects of the present concepts. The posts 122' have a trapezoidal shape. Thus, the outer edge 134' is longer than the inner edge 136'. Further, the side edges 138' are the same length. According to the dimensions and ranges of dimensions provided above, the length of the outer edge 134'—also described as the distance $D_7'$—can be, for example, about 1.20 mm to about 1.30 mm, such as about 1.25 mm. The length of the inner edge 136'—also described as the distance $D_8'$—can be, for example, about 0.65 mm to about 0.75 mm, such as about 0.70 mm. The length of the side edges 138'—also described as the distance $D_9'$—can be, for example, about 0.50 mm to about 0.60 mm, such as about 0.55 mm. For these distances, the angle $\theta_1'$ between the outer edge 134' and the side edges 138' can be, for example, about 10° to about 170°, such as about 60°. Further, the angle $\theta_2'$ between the inner edge 136' and the side edges 138' can be, for example, for example, about 10° to about 170°, such as about 120°.

Figure 1H:
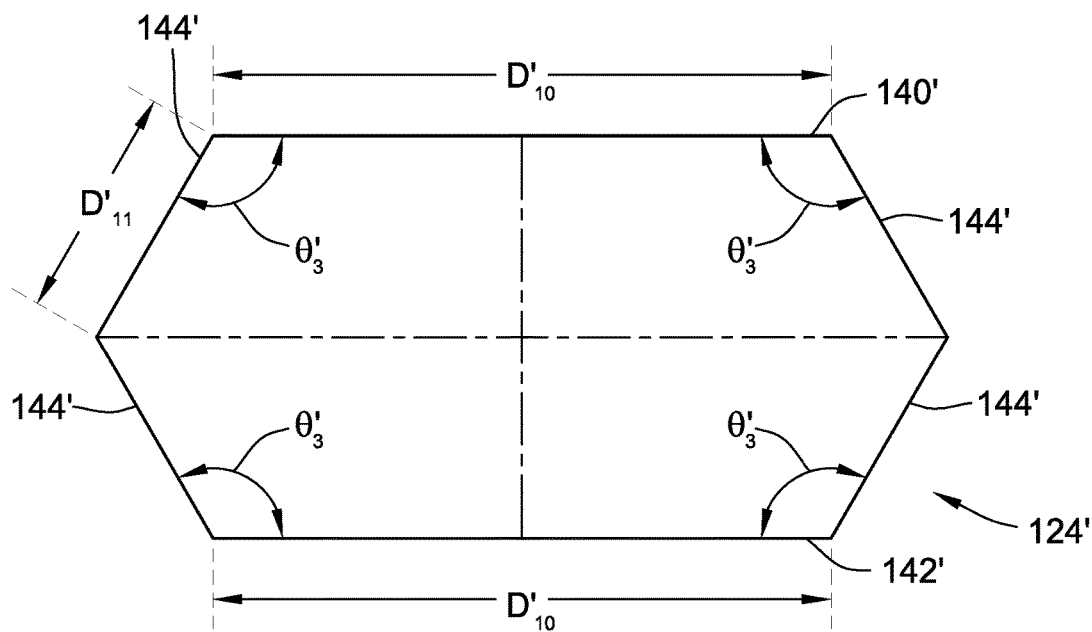
FIG. 1H illustrates a plan view of another post within the alternative chamber of FIG. 1F, in accord with some aspects of the present concepts.

FIG. 1H illustrates a plan view of the posts 124' within the device 100, in accord with some aspects of the present concepts. The posts 124' have a hexagonal shape. Thus, the outer edge 140' is about the same length as the inner edge 142'. Further, the side edges 144' are the same length. According to the dimensions and ranges of dimensions provided above, the lengths of the outer edge 140' and the inner edge 142'—also described as the distance $D_{10}'$—can be, for example, about 0.85 mm to about 0.95 mm, such as about 0.90 mm. The length of the side edges 144'—also described as the distance $D_{11}'$—can be, for example, about 0.30 mm to about 0.40 mm, such as about 0.35 mm. For these distances, the angle $\theta_3'$ between the outer edge 140', or the inner edge 142', and the side edges 144' can be, for example, about 10° to about 170°, such as about 120°.

Based in part on the material used to form the posts 122 and 124 (or posts 122' and 124'), as described above, fluid that contacts the posts 122 and 124 exhibits a specific contact angle relative to the surfaces of the posts 122 and 124. The contact angle is, in part, based surface tension of the fluid. The contact angle is also, in part, based on the interaction at the molecular level between the fluid and the material of the posts 122 and 124, or at least on the external surfaces of the posts 122 and 124. For example, for water on PDMS, the contact angle can be about 20° to about 110°. The variation can occur based on surface functionalization. Thus, the contact angles of the fluids that contact the posts 122 and 124 can be used to constrain the fluids as desired by the arrangement of the posts 122 and 124.

In particular, for fluid to become constrained by a geometric feature, such as the posts 122 or 124, or the gaps between the posts 122 and 124, the angles of the posts 122 or 124 are configured to be larger than the contact angle of the fluid on the surface of the posts 122 or 124. Thus, fluid that contacts the outer edge 134 of the post 122 is required to bend around the large angle (e.g., 300°) at the corners of the outer edge 134 and the side edges 138. Similarly, fluid that contacts the inner edge 136 of the post 122 is required to bend around the large angle (e.g., 240°) at the corners of the inner edge 136 and the side edges 138. Similarly, fluid that contacts the outer edge 140 (or the inner edge 142) of the post 124 is required to bend around the large angle (e.g., 240°) at the corners of the outer edge 140, or the inner edge 142, and the side edges 144. By requiring the fluid to bend around a corner having a large angle, capillary action becomes reduced or halted and higher fluid pressures are required to burst through the constraining feature. As applied to the chamber 120, the constraining features become the adjacent posts 122 and adjacent posts 124 within the rings 122a and 124a, respectively.

Indeed, the contact angle for any fluid or material on the surfaces of the posts 122 and 124 can be modified based on surface functionalization of the posts 122 and 124. In some aspects, the surface functionalization can include molecules on the surfaces of the posts 122 and 124 that promote cross-linking with one or more of the fluids that are loaded into the chamber 120. The surface functionalization can alternatively include embedded magnetic particles and/or generated magnetic fields, such as from external electromagnets, to interface with magnetic solids within the fluids. The surface functionalization can also include increasing the surface roughness of the posts 122 and 124. Surfaces can also be modified using plasma treatment or other means of oxidizing a material, deposition of a coating that modifies the surface properties, and similar means. Additionally, the fluid properties can be modulated through the addition of surfactants, particles, or application of electric fields to change the surface tension.

Based on the foregoing geometries of the posts 122 and 124, in addition to the materials used to form the posts 122 and 124 (or at least at the surfaces of the posts 122 and 124), fluid flows past the posts 122 and/or 124, or is retained by the rings 122a and/or 124a formed by the posts 122 and/or 124. Fluid entering the chamber 120 from the inlet channel 114 is constrained by the outer edges 134 of the posts 122. By being constrained, the fluid can be guided and/or forced to flow within the chamber channel 128 between the wall of the chamber 120 and the ring 122a of posts 122. Further, fluid between the rings 122a and 124a, as defined by the posts 122 and 124, respectively, can be constrained by the geometries of the posts 122 and 124 and remain within the chamber ring 130. Thus, fluid loaded within the chamber ring 130, such as by pipetting or other methods, can remain within the chamber ring 130, even with fluid flowing past within the chamber channel 128. As a further example, fluid within the ring 124a is constrained by the geometries of the posts 124 and remains within the chamber well 132. Thus, fluid loaded within the chamber well 132, such as by pipetting or other methods, can remain within the chamber well 132, even with fluid within the chamber ring 130. Different fluids within the chamber channel 128, the chamber ring 130, and the chamber well 132 can be separated and/or constrained from each other further based on, for example, differences in viscosities, solubility, densities, etc. of the fluids. Thus, a combination of the shapes and surface functionalities of the posts 122 and 124, in combination with one or more properties of the fluids within the chamber 120 (e.g., within the chamber channel 128, the chamber ring 130, and the chamber well 132) promote and/or inhibit the fluids from mixing and allow different flow channels, rings, and/or wells to be formed within the chamber 120 having different fluids therein.

In some aspects, differences in, for example, the viscosities, solubility, densities, etc. of the fluids used can allow for different fluids to be loaded into the same chamber ring 130 or chamber well 132. For example, fluids having different viscosities can be loaded at different locations within the chamber ring 130. A first fluid can be loaded in the first quadrant of the chamber ring 130, a second fluid can be loaded in the second quadrant of the chamber ring 130, a third fluid can be loaded into the third quadrant of the chamber ring 130, and a fourth fluid can be loaded into the fourth quadrant of the chamber ring 130. Based, in part, one the geometries and surface functionalization of the posts 122 and 124, in addition to the differences in one or more properties of the four fluids, each fluid remains within the chamber ring 130 without mixing and without escaping during fluid flow within the chamber channel 128.

In some aspects, the positions of, for example, the inlet port 106 and the outlet port 110, as well as, for example, the flow rate of the fluid, allow for the flow of fluid through the chamber channel 128 without requiring that the chamber channel 128 be closed or covered. In alternative aspects, the chamber channel 128, or any other channel within the chamber 120 that allows fluid to flow through the chamber 120, can be closed or covered to promote and/or allow fluid flow through the chamber channel 128. The channel can be closed based on the base 102 or the lid 104 covering the channel.

Figure 1I:
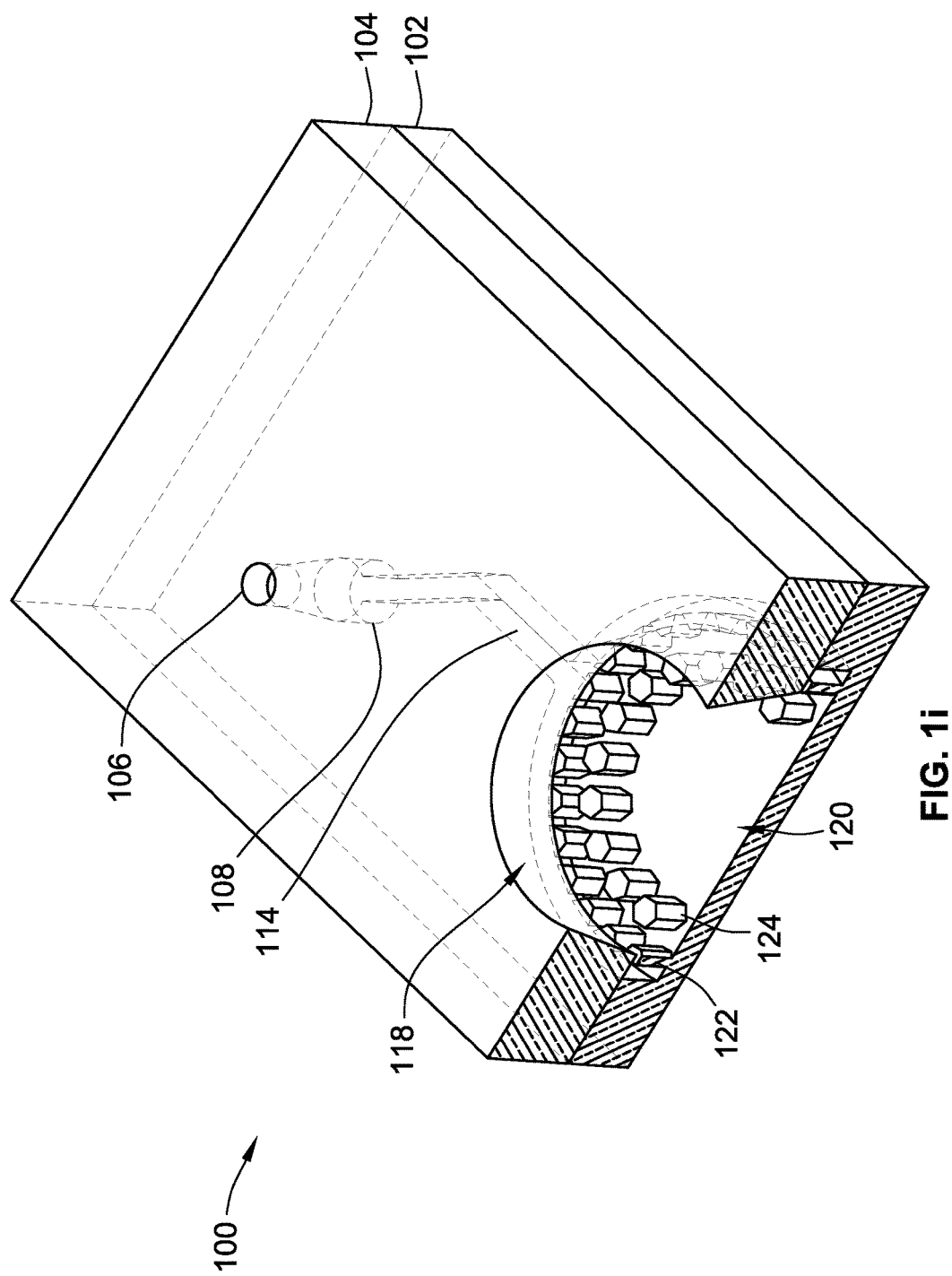
FIG. 1I illustrates a partial perspective view of the radial microfluidic device of FIG. 1A, in accord with some aspects of the present concepts.
Figure 1J:
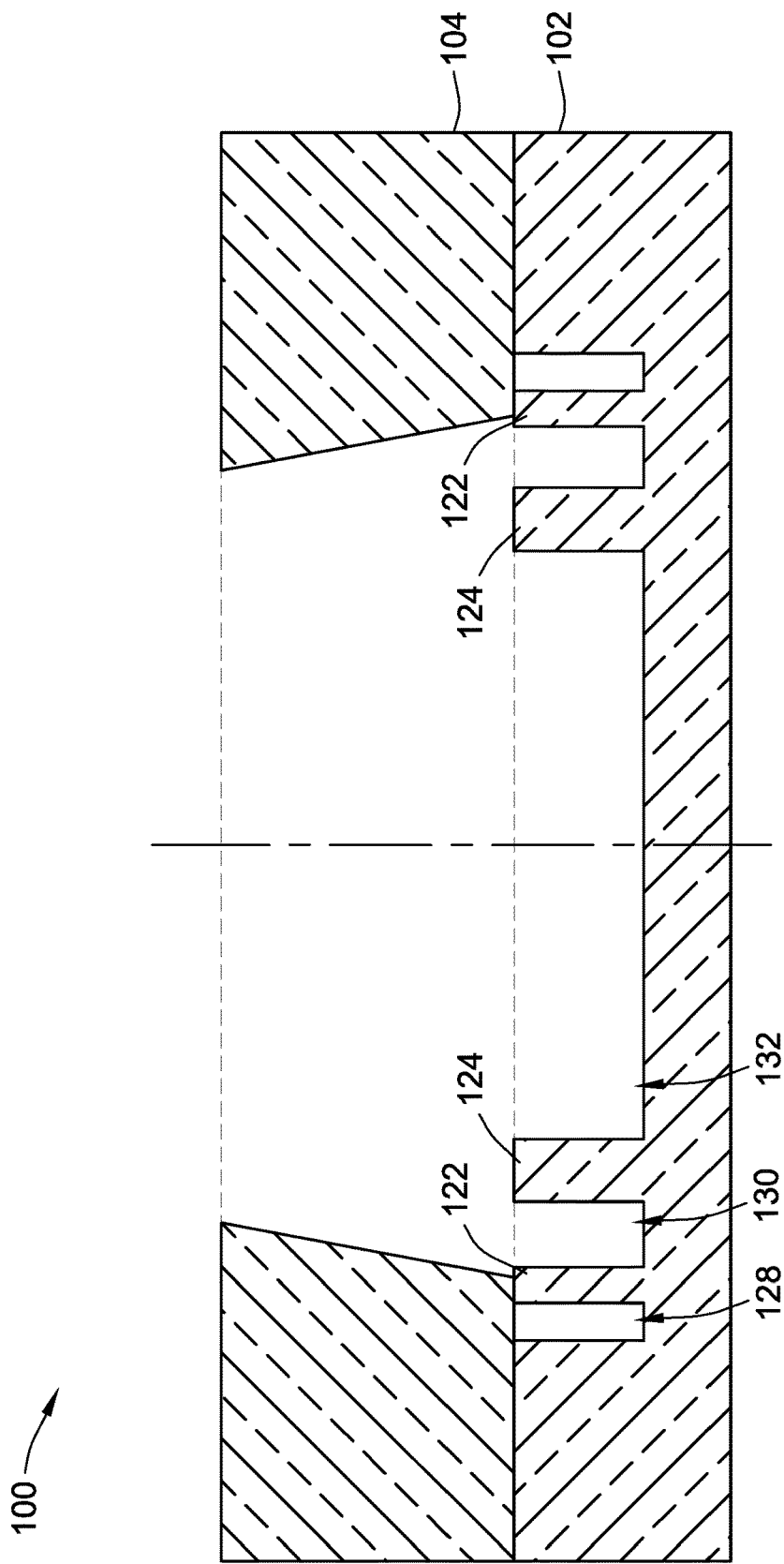
FIG. 1J illustrates a cross-sectional slice of the radial microfluidic device of FIG. 1A, in accord with some aspects of the present concepts.
Figure 1K:
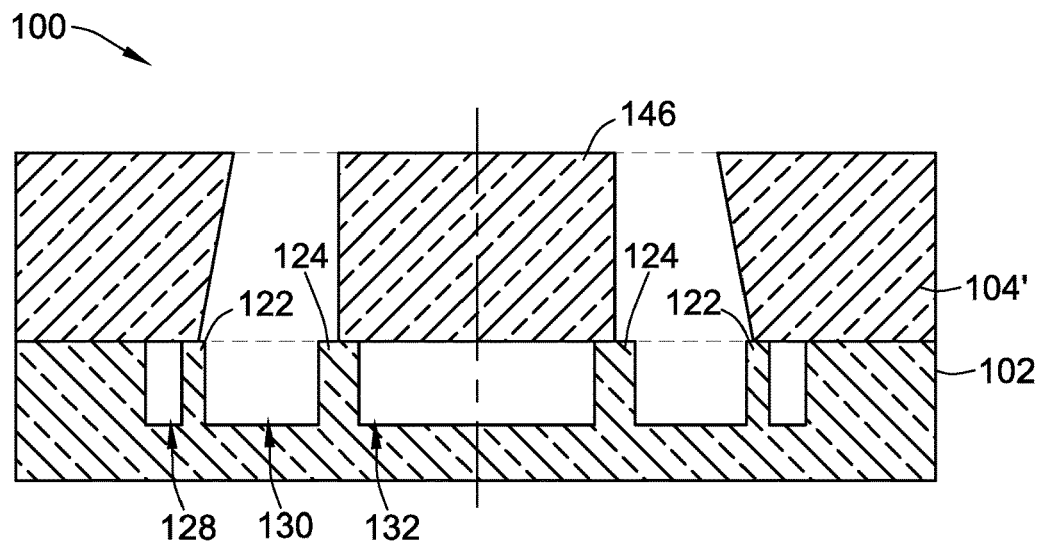
FIG. 1K illustrates a cross-section slice of the radial microfluidic device of FIG. 1A with an alternative lid, in accord with some aspects of the present concepts.

FIG. 1I illustrates a cross-sectional slice of the device 100, in a perspective view, in accord with some aspects of the present concepts. Further, FIG. 1I illustrates a cross-sectional slice of the device 100, in accord with some aspects of the present concepts. As shown, the edge of the lid 104 that defines or surrounds the opening 118 is aligned with and contacts the posts 122 (or ring 122a). Accordingly, the lid 104 covers the chamber channel 128. In cases where the lid 104 is removable, the lid 104 can be removed from the base 102 to provide access to the chamber channel 128.

In some aspects, the edge of the lid 104 that defines or surrounds the opening 118 instead can be aligned with and contact the posts 124, to cover the chamber ring 130, or partially overhang above the chamber well 132. In some aspects, the lid 104 can include one or more portions that cover additional sections of the chamber 120, while leaving remaining sections of the chamber 120 uncovered.

Figure 1L:
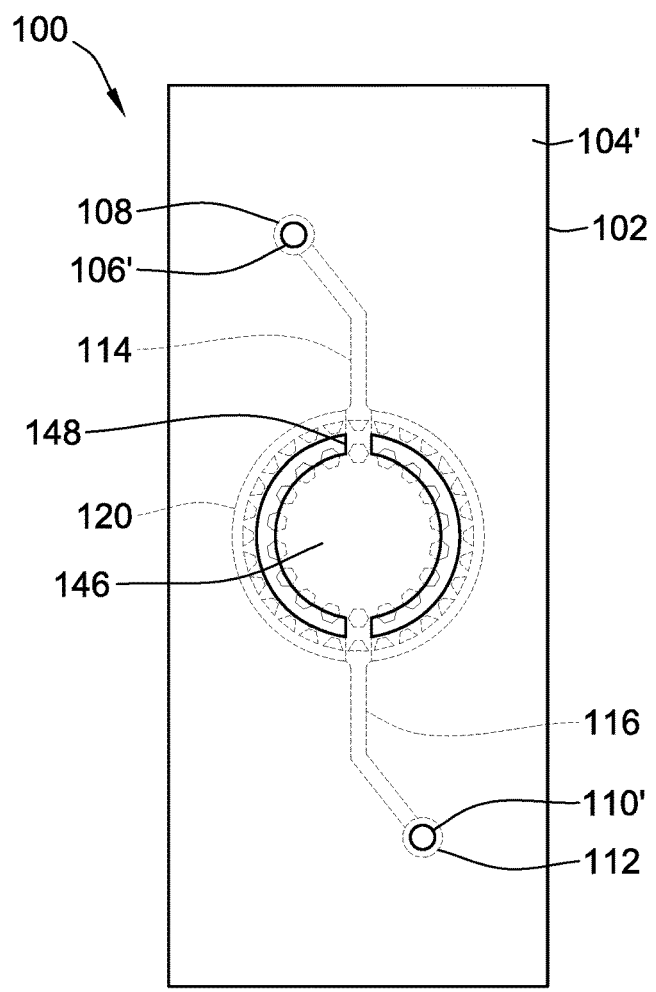
FIG. 1L illustrates a top view of the radial microfluidic device of FIG. 1K, in accord with some aspects of the present concepts.

FIG. 1L illustrates a cross-sectional slice of the device 100 with an alternative configuration of the lid 104' covering the base 102, in accord with some aspects of the present concepts. FIG. 1I illustrates a plan view with the lid 104' covering the base 102, in accord with some aspects of the present concepts. As shown, the lid 104' can include an island 146 that is arranged to cover the chamber well 132. However, the opening 118' of the lid 104' still provides for the chamber ring 130 to remain uncovered. As illustrated in FIG. 1L, the lid 104' can include one or more bridges 148 that connect the island 146 to the remainder of the lid 104'. Thus, the configuration of the lid 104' can to cover additional and/or alternative areas of the chamber 120, as desired for the specific purposes of the device 100.

Figure 2:
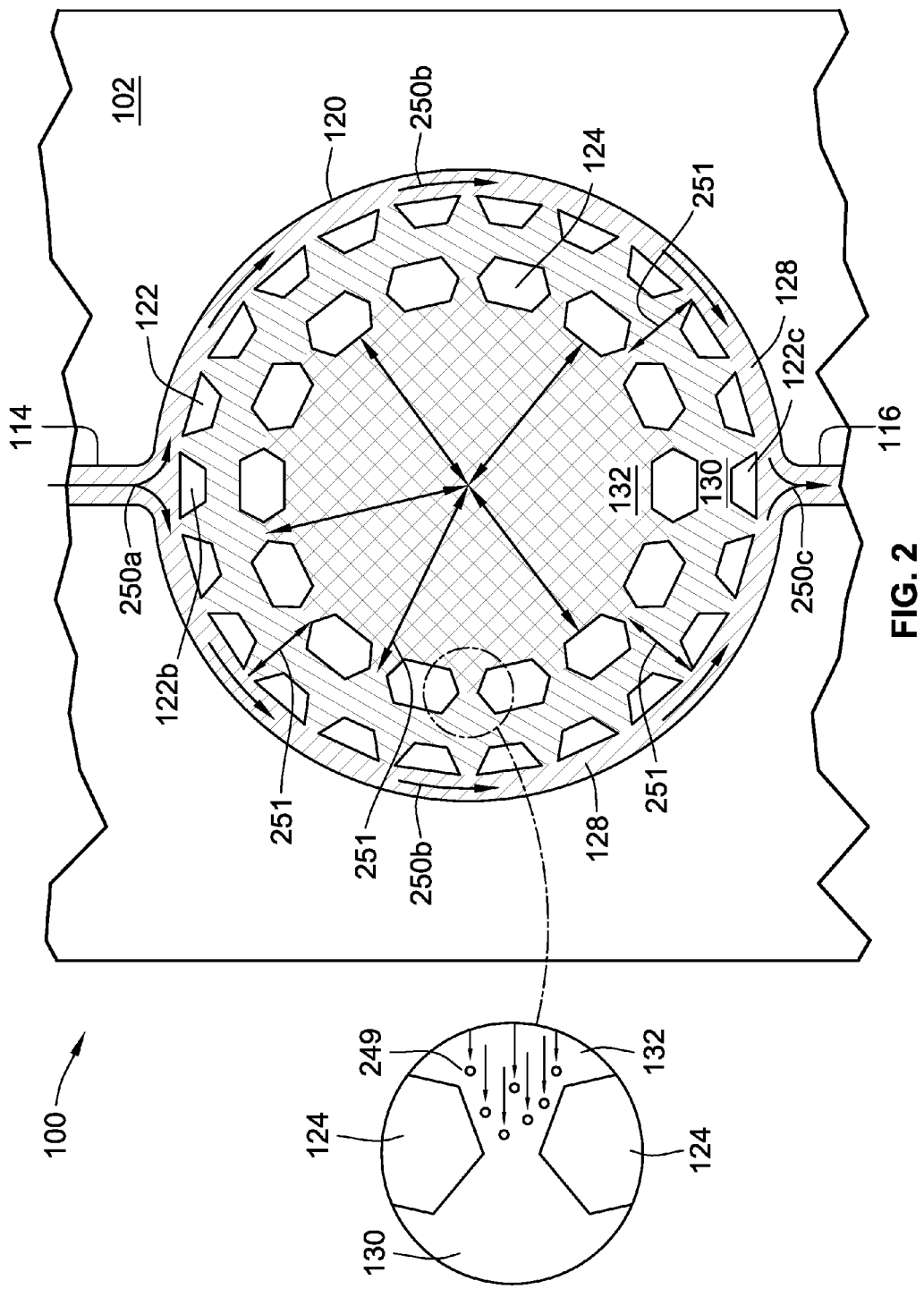
FIG. 2 illustrates a detailed top view of fluid flow within the chamber of the radial microfluidic device of FIG. 1A, in accord with some aspects of the present concepts.

FIG. 2 illustrates a detailed top view of fluid flow within the chamber 120 of the device 100, in accord with some aspects of the present concepts. As described above, the chamber 120 includes the chamber channel 128. The chamber channel 128 is in fluid communication with the inlet channel 114 and the outlet channel 116. Fluid flows into the chamber 120 from the inlet channel 114 and is constrained within the chamber channel 128 based on the geometry and, optionally, the surface functionalization of the posts 122 and the wall of the chamber 120. As illustrated, one of the posts 122 (e.g., post 122b) is positioned at the entrance of the inlet channel 114 to the chamber 120. The post 122b positioned at the entrance of the inlet channel 114 aids in transitioning the radial flow of fluid from the inlet channel 114 to a circumferential flow of fluid within the chamber channel 128. For example, the post 122b positioned at the entrance of the inlet channel 114 blocks fluid from flowing further towards a center of the chamber 120, rather than flowing within the chamber channel 128. In some aspects, the flow of fluid from the inlet channel 114 can be about 5 microliters per hour to about 400 microliters per hour, such as about 200 microliters per hour. However, this flow rate can vary depending on, for example, the overall dimensions of the device 100. The transition of the fluid flow from that of a radial flow out of the inlet channel 114 to a circumferential flow within the chamber channel 128 is represented by the divided arrow 250a. The fluid flow then proceeds within the chamber channel 128 circumferentially around the posts 122, as represented by the arrows 250b. Moreover, the post 122b also aids in providing uniform fluid flow on each side of the ring 122a of posts 122, which provides for stable and defined radial gradients 251 to form within the chamber ring 130 and/or the chamber well 132, as discussed in greater detail below.

Similarly, one of the posts 122 (e.g., post 122c) is positioned at the entrance of the outlet channel 116 to the chamber 120. The post 122c positioned at the entrance of the outlet channel 116 aids in transitioning the circumferential flow of the fluid within the chamber channel 128 to a radial flow into the outlet channel 116. For example, the post 122c positioned at the entrance of the outlet channel 116 blocks fluid from flowing towards the center of the chamber 120, rather than flowing into the outlet channel 116. The transition of the fluid flow from that of a circumferential flow within the chamber channel 128 to a radial flow into the outlet channel 116 is represented by the merged arrow 250c. The fluid flow then proceeds within the outlet channel 116.

The chamber 120 also includes the chamber ring 130. The chamber ring 130 can be loaded with one or more fluids. The one or more fluids can be loaded through the opening 118 in the lid 104, or by removal of the lid 104 from the base 102. As described above, the one or more fluids can include solids, such as suspended solids, dissolved solids, powdered or granular solids, pre-shaped solids, and the like. Although described as a fluid, the material within the chamber ring 130 can be a semi-solid, such as a gel, or a solid, such as a polymerized, cross-linked, fused, or annealed material. In addition to the geometry and, optionally, the surface functionalization of the posts 122 and 124, the viscosity of the gel can further aid in constraining the gel within the chamber ring 130. The large angles on the posts 122 and 124 at the openings between adjacent posts 122 and 124 constrain the gel in place because the contact angle of the gel on the surfaces of the posts 122 and 124 is smaller than the angle created between adjacent posts 122 and 124. As illustrated, the semi-solid is generally constrained between the outer edge 134 of the posts 122 and the centers of the posts 124.

The chamber 120 further includes the chamber well 132. The chamber well 132 can be loaded with one or more fluids. The one or more fluids can be loaded through the opening 118 in the lid 104, or by removal of the lid 104 from the base 102. Like the chamber ring 130, the chamber well 132 can contain one or more fluids that contain one or more solids, such as suspended solids, dissolved solids, and the like. Although described as a fluid, the material within the chamber well 132 also may be a semi-solid, such as a gel. In addition to the geometry and, optionally, the surface functionalization of the posts 124, the viscosity of the semi-solid can further aid in constraining the semi-solid within the chamber well 132. The large angles on the posts 124 at the openings between adjacent posts 124 constrain the semi-solid in place because the contact angle of the fluid on the surfaces of the posts 124 is smaller than the angle created between adjacent posts 124. As illustrated, the semi-solid is generally constrained between the centers of the posts 124.

With the device 100 as described above, one or more fluids can be loaded (e.g., pipetted) into the chamber well 132. The one or more fluids can be loaded through the opening 118 in the lid 104, or by removal of the lid 104 from the base 102. The one or more fluids can include collagen that contains hematopoietic stem cells, such as cord blood cells. The collagen and cord blood cells may initially be within a fluid matrix to make the overall fluid of the fluid matrix, collagen, and cord blood cells easier to load into the chamber well 132, such as easier to pipette. Once the overall fluid is loaded into the chamber well 132, the fluid matrix is allowed to evaporate, or the solution is allowed to set, such that the remaining components (e.g., collagen) become gelatinous.

Various fluids can be loaded into the chamber well 132. These fluids include, for example, biopolymers, such as collagen and/or a gelatinous protein mixture, alginate, polyacrylamide, cell culture mediums, hydrogels from biopolymers or synthetic organic polymers, blood, bone marrow, interstitial fluid, urine, fecal matter, and the like. The specific fluids used can vary depending on the specific biological system for which the device 100 is intended to mimic. Within the fluids can include various ions, factors, nutrients, cells, cell media, bone matrix powder, sensing particles (for ions, pH, oxygen, proteins, etc.), particles to modulate the viscosity or viscoelasticity of the fluid, and the like. With the fluid and material within the chamber well 132 as described, the chamber well 132 can be used to mimic biological systems including, for example, bone marrow, vascularization of implants or tissue engineering products, three-dimensional organs of various types, the lining of the gut, muscle, plant tissues (e.g., stem architecture), and other biological systems.

Similarly, one or more fluids can be loaded (e.g., pipetted) into the chamber ring 130. For example, the one or more fluids can include a gelatinous protein mixture, such as MATRIGEL® by Corning Incorporated, and the fluid can contain human umbilical vein endothelial cells (HUVECs), bone powder or bone matrix powder, mesenchymal stem cells (MSCs), fluids containing growth factors or drugs and other compounds, particles to further provide distinct microenvironments for cell growth, collagen, fibronectin, starches and other polysaccharides, and the like. The specific fluids used can vary depending on the specific biological system for which the device 100 is intended to mimic. As with the chamber ring 130, the gelatinous protein mixture, HUVECs, and bone powder may initially be within a fluid matrix to make the overall solution easier to load into the chamber ring 130, such as easier to pipette. Once the fluid is loaded into the chamber ring 130, the fluid matrix is allowed to evaporate, or the solution is allowed to set, such that the remaining components (e.g., gelatinous protein mixture) become gelatinous. Fluid can additionally be set in place by polymerization of the components in the fluid (e.g., polyacrylamide using UV or chemical initiation), thermally (e.g., collagen forming fibrils above 4° C.), chemically (e.g., ammonium persulfate-initiated radical polymerization), or ionically (e.g., alginate gelling when exposed to calcium).

The containment or constraint of the one or more fluids by the posts 122 and 124 allows for the creation of membranes and extracellular scaffolds with defined shapes and dimensions on the micrometer scale. In particular, fluid can be loaded into, for example, the chamber ring 130, and the fluid can be allowed to set. Upon the fluid setting, the material within the fluid can create a membrane and/or an extracellular scaffold. The membrane and/or extracellular scaffold can mimic a cross-section of a lumen found in an organism. Thus, a membrane can be generated within the chamber ring 130, at the interfaces of the chamber ring 130 and the chamber well 132, and/or the chamber channel 128 and the chamber ring 130. The membrane is generated in situ based on the fluid being loaded within the chamber ring 130 and allowing the fluid to set. Thus, a pre-fabricated ring is not required. The posts 122 and 124 also allow for the ability to use one or more fluids to create the membranes and extracellular scaffolds. The use of one or more fluids provides the ability to use gradients of fluids, such as gels, of different types, densities, resulting stiffness, and porosity by forming gels in close apposition using two or more different arrays of posts (e.g., posts 122 and 124). In some cases, after forming the membrane within the chamber ring 130, the membrane can be seeded with biological tissues and/or cells. In some aspects, fluid can be flowed through the chamber channel 128 to cause vascularization within the membrane. For example, vascularization can occur by flowing endothelial cells in the chamber channel 128, allowing them to attach to surfaces, including the interface between the chamber channel 128 and the chamber ring 130, and then allowing them to grow. To aid this, it can be advantageous to add VEGF or other signaling or growth factors to generate a gradient between the chamber channel 128 and the chamber ring 130 or the chamber well 132 to allow the cells to respond. Vascularization can also be accomplished by pipetting endothelial cells into the chamber ring 130 or the chamber well 132. These vascularization methods may be helpful for testing various vascularization strategies, including drugs to aid vascularization, for tissue or device implants. As another example, fluid with seeding cells and/or growth factors can be flowed through the chamber channel 128 to contact the membrane within the chamber ring 130. Fluid within the chamber well 132 further can be used to seed the membrane and/or cause vascularization to occur within the membrane. When developing the device 100, such as developing one or more cells and/or cell layers within the device 100 on the exterior and/or interior of the chamber ring 130, or with the chamber well 132, tissue-culturing working fluids can be passed through the chamber channel 128 and/or loaded into the chamber ring 130 and/or the chamber well 132.

In some aspects, and as described above, the posts 122 and 124 used to define the chamber ring 130 and form the membrane can dissolve and/or degrade after forming the membrane. The membrane itself can dissolve the posts 122 and 124. Alternatively, fluid can be flowed through the chamber channel 128 to dissolve the posts 122 and 124. Alternatively, the posts 122 and 124 may biodegrade. As a result, the membrane can remain, and radial gradients 251 that form within the chamber well 132 and/or the chamber ring 130 within the membrane will not be restricted by the presence of the posts 122 and 124. For example, with the posts 122 and 124 gone after formation of the membrane, the posts 122 and 124 will not impede diffusion and/or cell migration within the device 100.

In some aspects, after gelling the chamber ring 130 and/or the chamber well 132, fluid can be flowed through the chamber channel 128. In alternative aspects, fluid can be flowed through the chamber channel 128 prior to fluid within the chamber ring 130 gelling. As a result f the geometry of the chamber 120, such as the generally circular chamber ring 130 and chamber well 132, radial gradients 251 can form between the chamber channel 128 and one or more of the chamber ring 130 and the chamber well 132. For example, components within the fluid flowed through the chamber channel 128 can be bound to cells within the chamber ring 130. This results in a low cell concentration at the center of the chamber well 132, and a progressively higher cell concentration near the chamber ring 130 as the cells (e.g., cells 249) are attracted to the components within the fluid in the chamber channel 128. Alternatively, the components within the fluid flowed through the chamber channel 128 can diffuse through a membrane within the chamber ring 130 and into the chamber well 132. Cells producing one or more factors at the center creates a radial gradient 251 with the concentration of the one or more factors being a maximum at the center of the chamber well 132, and the concentration of the one or more factors being a minimum at the edges of the chamber well 132 or the outer edges of the chamber ring 130. Alternatively, or in addition, cells or any component contained within fluid flowed within the chamber channel 128 can migrate towards cells or any other component within the chamber ring 130 and/or the chamber well 132, cells or any component contained within fluid within the chamber well 132 can flow towards cells within the chamber channel 128 and/or the chamber ring 130, or a combination thereof. Accordingly, the device 100 is configured to simulate one or more biological functions that typically include cellular communication between the chamber channel 128 and the chamber ring 130 and/or the chamber well 132, as would be experienced in-vivo within organs, tissues, cells, etc., and particularly concentric tissues and/or tubes (e.g., tubes within tubes). Depending on the application, the membrane created within the chamber ring 130 is designed to have a porosity to permit the migration of cells, particulates, media, proteins, and/or chemicals between the chamber channel 128 and the chamber well 132, as desired for the specific biological system for which the device 100 is intended to mimic.

In some aspects, the radial gradients 251 are symmetric when the flow of fluid and the introduction of components within the fluid into the device 100 is at a steady-state. The symmetric gradients 251 can be formed because of the uniform flow of fluid within the chamber 120, as well as the symmetric features within the chamber 120, such as the concentric chamber channel 128, chamber ring 130, and chamber well 132. In some aspects, however, asymmetric gradients can be formed based on non-uniform flow that can be generated based on variations to the radial microfluidic device 100 discussed below. Additionally, asymmetric gradients can be generated based on, for example, asymmetric features within the chamber 120, such as by having one or more eccentric chamber channel 128, chamber ring 130, and/or chamber well 132 within the chamber 120.

Figure 3:
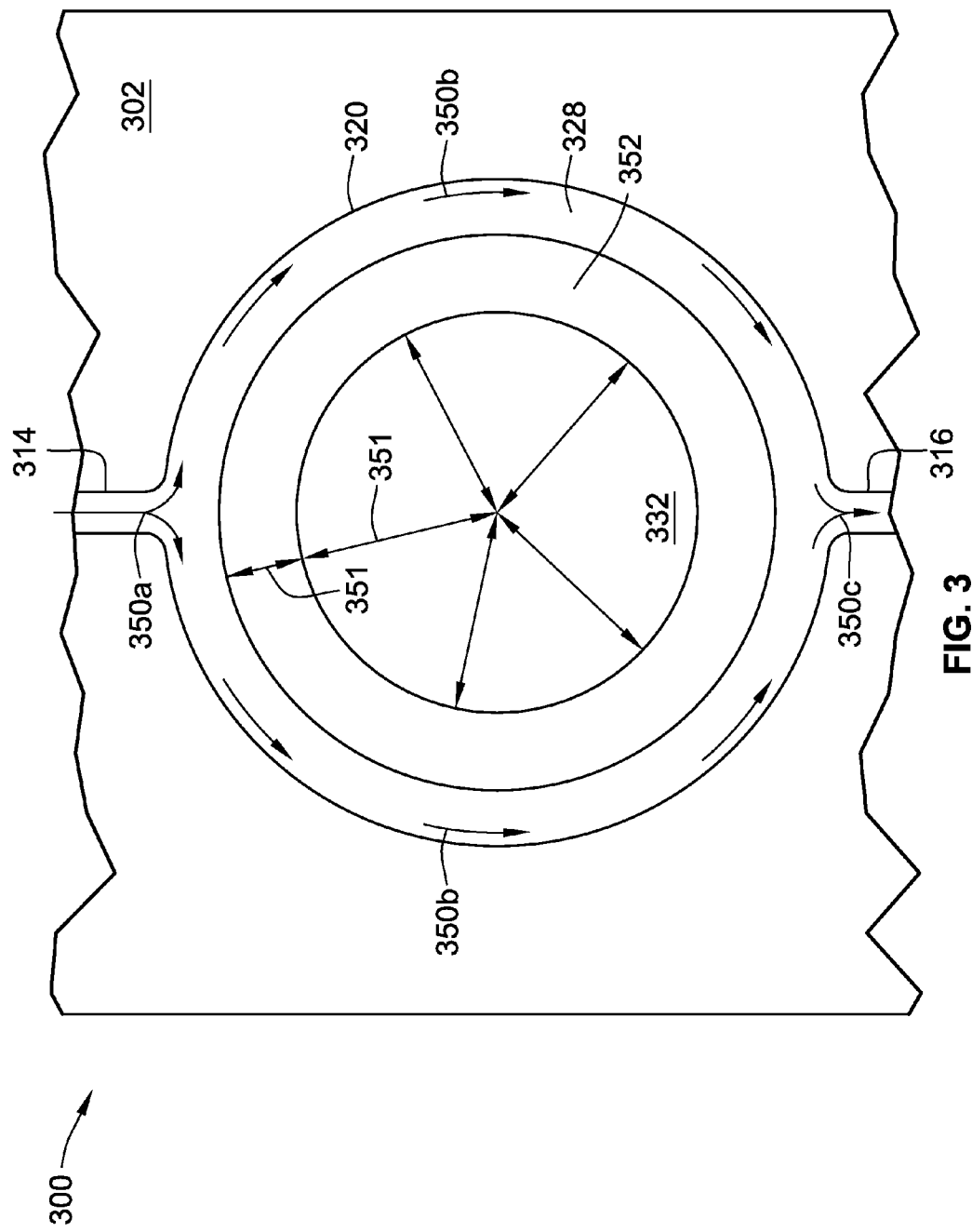
FIG. 3 illustrates a detailed top view of an alternative radial microfluidic device, in accord with some aspects of the present concepts.

FIG. 3 illustrates a detailed top view of an alternative chamber 320 within a radial microfluidic device 300, in accord with some aspects of the present concepts. The device 300 is generally the same as the device 100 described above. Therefore, like reference numerals correspond to like features. However, the device 300 includes the following differences relative to the device 100. Specifically, the chamber 320 of the device 300 excludes posts 122 and 124. Instead, a membrane 352 can be fabricated outside of the device 300 and inserted into the chamber 320. The membrane 352 can replace the chamber ring 130, as well as the posts 122 and 124 used to form the chamber ring 130. Although fabrication of the membrane 352 is not in situ, the membrane 352 can still separate the chamber 320 into a chamber channel 328 and a chamber well 332. Fluid can be flowed around the membrane 352 within the chamber channel 328. Specifically, fluid is radially flowed into the chamber channel 328 from the inlet channel 314, where it interfaces with the membrane 352 and is caused to flow circumferentially around the membrane 352, as represented by the arrows 350a. The fluid then flows circumferentially around the membrane 352 within the chamber channel 328, as represented by the arrows 350b. As discussed above, a lid (not shown) can be aligned with and contact the membrane 352 so as to cover the chamber channel 328 to prevent the fluid from overflowing over the wall of the chamber 320 or the membrane 352. The fluid then flows out of the chamber channel 328 and into the outlet channel 316, as represented by the merged arrows 350c. Although the membrane 352 is fabricated outside of the device 300, the membrane 352 also allows for radial gradients 351 to form within the device 300, and specifically within the chamber well 332 and/or the membrane 352 itself, based on the circumferential flow of fluid around the membrane 352 and the fluid within the chamber well 332.

In some aspects, the membrane 352 can be formed in situ without the use of the posts 122 and 124. Instead, the chamber 320 can include a removable mold (not shown). The removable mold can be used similar to the chamber 120 with posts 122 and 124. Specifically, the mold can be used to divide the chamber 320 into one or more section, such as sections corresponding to the chamber ring 130 and the chamber well 132. However, after the fluid(s) have been set, forming, for example, the membrane 352, the mold can be removed from the chamber 320, leaving the membrane 352.

Figure 4:
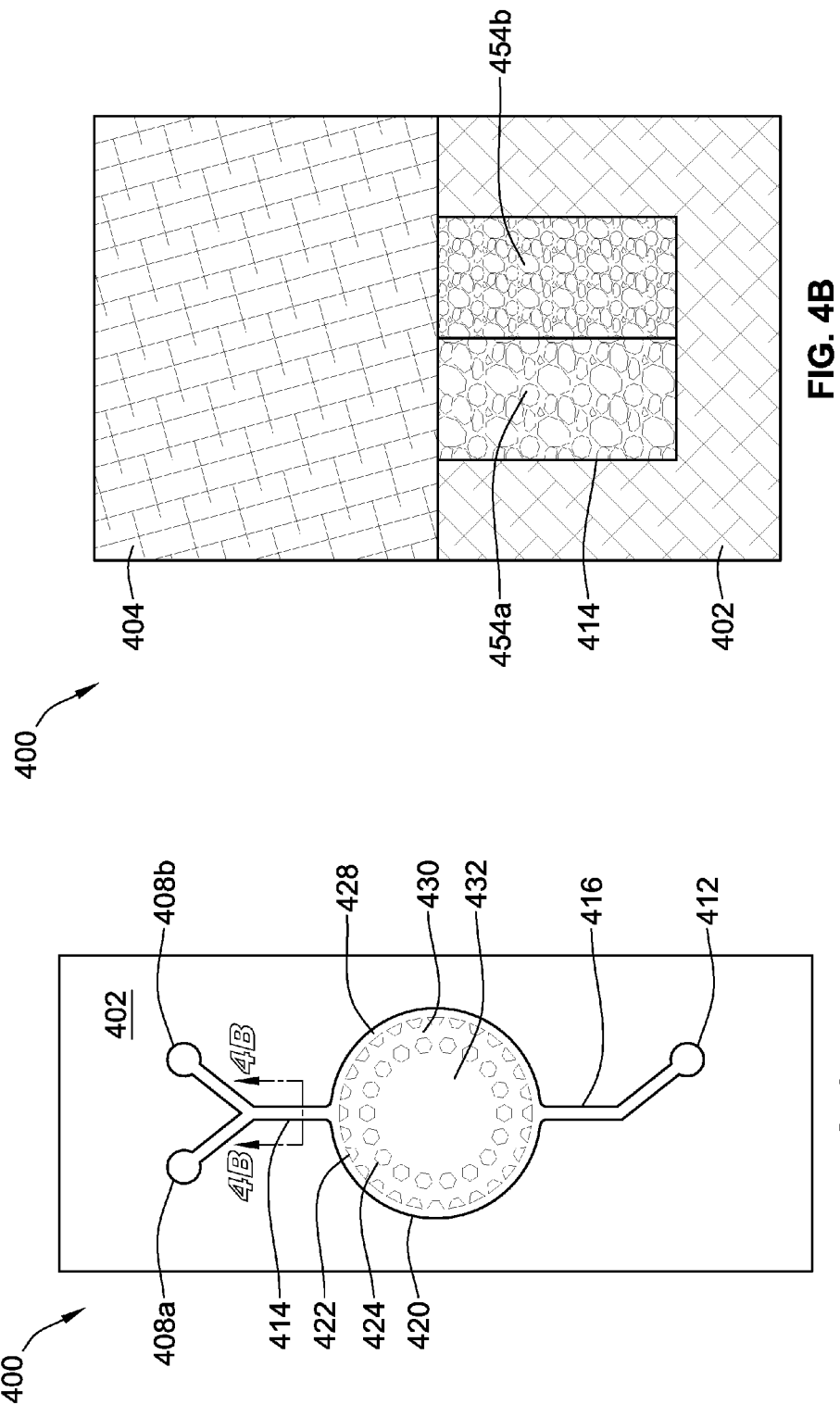
FIG. 4A illustrates a top view of an alternative radial microfluidic device, with a lid removed, in accord with some aspects of the present concepts.
FIG. 4B illustrates a cross-sectional view of an inlet channel of the radial microfluidic device of FIG. 4A, in accord with some aspects of the present concepts.

FIG. 4A illustrates a top view of an alternative radial microfluidic device 400, with the lid not illustrated, in accord with some aspects of the present concepts. The device 400 is generally the same as the device 100 described above. Therefore, like reference numerals correspond to like features. However, the device 400 includes the following differences relative to the device 100. Specifically, instead of having a single fluid inlet 108, the device 400 includes fluid inlets 408a and 408b. Although not shown, the corresponding lid of the device 400 also has corresponding inlet ports that each align with one of the fluid inlets 408a and 408b. The fluid inlets 408a and 408b allow for the device 400 to connect to different fluid sources, or multiple fluid lines from the same fluid source. Further, the fluid inlets 408a and 408b connect to the same inlet channel 414. By both fluid inlets 408a and 408b connecting to the same inlet channel 414, linear gradients can be formed in the fluid entering the chamber 420. More specifically, fluids from two fluid sources that connect to the fluid inlets 408a and 408b can be combined within the inlet channel 414 to form a single stream of fluid. The single stream of fluid can include two different fluids (e.g., fluid matrixes), or two of the same fluid but having different concentrations of one or more components (e.g., different cell concentrations).

FIG. 4B illustrates a cross-sectional view of the inlet channel 414 of the device 400 of FIG. 4A along the line 4B-4B, in accord with some aspects of the present concepts. More specifically, the cross-sectional view of the inlet channel 414 shows the inlet channel 414 downstream from where fluid 454a, inputted through the fluid inlet 408a, and fluid 454b, inputted through the fluid inlet 408b, combine within the inlet channel 414. Based on, for example, the flow rates, the viscosities, the densities, the chemistries, the turbulence, etc. of the fluids 454a and 454b, and/or flow of the fluids 454a and 454b, the fluid 454a can be substantially separated from the fluid 454b within the inlet channel 414. Accordingly, when the fluid stream shown in FIG. 4B enters the chamber 420, the fluid 454a flows substantially counterclockwise around the chamber 420 and within the chamber channel 428, and the fluid 454b flows substantially clockwise around the chamber 420 and within the chamber channel 428. By being able to flow two different fluids 454a and 454b within the chamber 420, different radial gradients can be generated within the chamber ring 430 and/or the chamber well 432 based on the differences in, for example, the properties, the chemistries, the components (e.g., cells, factors, etc.) of the fluids 454a and 454b. For example, the fluid 454a flowing the left side of the chamber ring 430 and the chamber well 432 can cause different radial gradients than the fluid 454b flowing on the right side of the chamber ring 430 and chamber well 432.

Alternatively, the fluids 454a and 454b can be the same fluid (e.g., fluid matrix), but may contain different concentrations of one or more components. The components can then mix within the inlet channel 414, prior to entering the chamber 420. For example, the fluid 454a does not include a cell growth factor, and the fluid 454b includes the cell growth factor at a concentration X. Upon the fluids 454a and 454b combining within the inlet channel 414, the fluids 454a and 454b at least partially mix, along with the components within the fluids 454a and 454b (e.g., the cell growth factor). The concentration X of the cell growth factor consequently varies from being lower on the left side of the inlet channel 414 to being higher on the right side of the inlet channel 414. The result is having a lower concentration of the cell growth factor on the left side of the chamber ring 430 and the chamber well 432, and a higher concentration of the cell growth factor on the right side of the chamber ring 430 and the chamber well 432. The variation in the concentration changes the gradients that form and can be used to determine the effects of the concentration within a single microfluidic device. Further, although only two fluid inlets 408a and 408b are illustrated, there may be more than two depending on the specifics of the radial microfluidic device that is desired, and the specifics of the tests to be performed using the microfluidic device.

Figure 5:
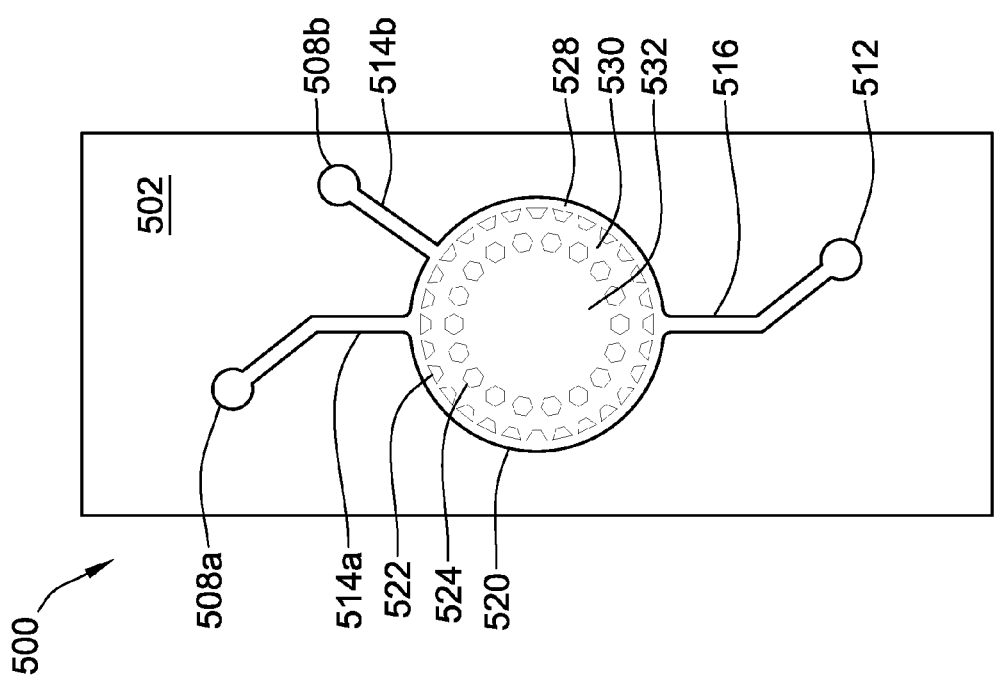
FIG. 5 illustrates a top view of an alternative radial microfluidic device, with a lid removed, in accord with some aspects of the present concepts.

FIG. 5 illustrates a top view of an alternative radial microfluidic device 500, with the lid not illustrated, in accord with some aspects of the present concepts. The device 500 is generally the same as the device 100 described above. Therefore, like reference numerals correspond to like features. However, the device 500 includes the following differences relative to the device 100. Specifically, instead of having a single fluid inlet 108, the device 500 includes fluid inlets 508a and 508b. Although not shown, the corresponding lid of the device 500 also has two corresponding inlet ports that align with the fluid inlets 508a and 508b. The fluid inlets 508a and 508b allow for the device 500 to connect to multiple and different fluid sources. Unlike the device 400, however, the fluid inlets 508a and 508b connect to different inlet channels. Specifically, the fluid inlet 508a connects to the inlet channel 514a, which is in fluid communication with the chamber 520. The fluid inlet 508b connects to the inlet channel 514b, which also is in fluid communication with the chamber 520. However, the inlet channel 514b is offset from the inlet channel 514a.

The arrangement of the fluid inlets 508a and 508b, in addition to the inlet channels 514a and 514b, allows for different fluids to be flowed through different portions of the chamber channel 528. Further, the inlet channel 514b can be moved relative to the inlet channel 514b. Further, although only two fluid inlets 508a and 508b and two inlet channels 514a and 514b are illustrated, there may be more than two of each depending on the specifics of the radial microfluidic device that is desired, and the specifics of the tests to be performed using the microfluidic device. In some aspects, the device 500 also can have more than one outlet channel 516, in addition to more than one fluid outlet 512 and outlet port 510.

In some aspects, the fluid flowing out of the device, such as any of the devices disclosed herein, can be analyzed to determine the components within the fluid. For example with respect to the device 500, the fluid flowing out of the outlet channel 516, the fluid outlet 512, and the outlet port 510 can be analyzed for determining the components within the fluid after passing through the device 500. In some respects, the device 500 can include more than one outlet channel, fluid outlet, and outlet port to provide fluid flow out of the device 500 at various locations. The fluid flow out of the device 500 at various locations provides insight into the components within the fluid at the various locations of the chamber channel 528. The insight can reveal, for example, differences in concentrations of the components within the fluid. The concentrations can vary depending on, for example, the length that the fluid has traveled within the chamber channel 528.

In some embodiments, rather than, or in addition to, including multiple outlet channels, the lid 504 of the device 500 can include one or more sample ports arranged above the chamber channel 528 and/or the chamber ring 530. The sample ports can be closed during normal operation but can be configured to accept an instrument to be inserted therein to access the chamber channel 528 and/or the chamber ring 530. The instrument can be, for example, a pipette or similar device that can withdraw fluid from the various sites along the chamber channel 528 and/or the chamber ring 530 through the sample ports. Like the description above with respect to the multiple outlet channels, the sample ports allow for sampling the fluid within the chamber 520 at various locations to determine the activity within the chamber 520. The various sampling can reveal, for example, gradients in the fluid based on the fluid flowing through the chamber channel 528. For example, a concentration of one or more components within the fluid can vary from the inlet channel 514a to the inlet channel 514b and/or the outlet channel 516. The concentration variations can be determined based on the sampling through the sample ports along the chamber channel 528.

Figure 6A:
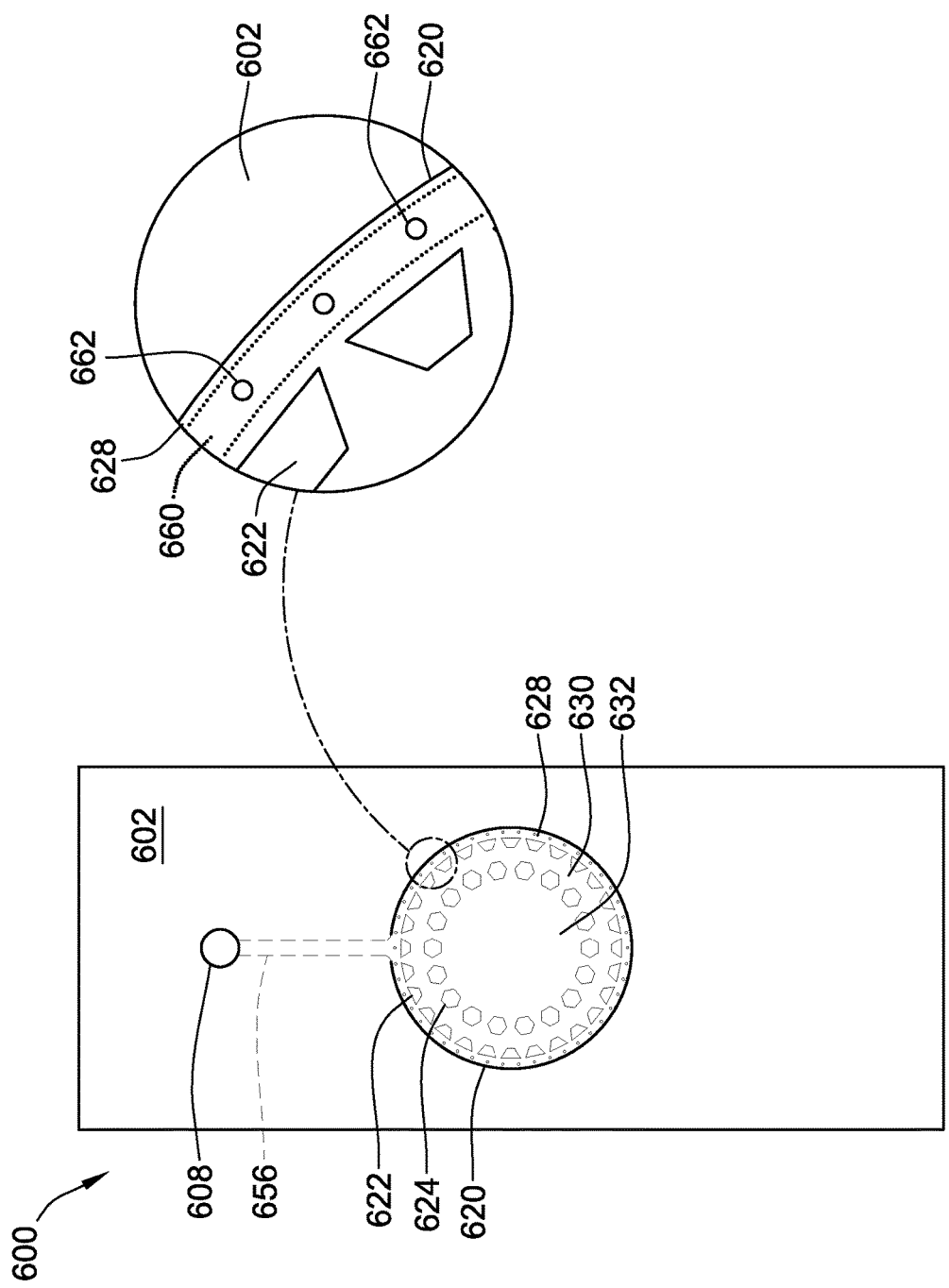
FIG. 6A illustrates a top view of an alternative radial microfluidic device, with a lid removed, in accord with some aspects of the present concepts.

FIG. 6A illustrates a top view of an alternative radial microfluidic device 600, with the lid not illustrated, in accord with some aspects of the present concepts. The device 600 is generally the same as the device 100 described above. Therefore, like reference numerals correspond to like features. However, the device 600 includes the following differences relative to the device 100. Specifically, the base 602 includes an inlet channel 656 that is covered by the base 602, such as a tunnel within the base 602. Thus, instead of, for example, the lid (not shown) closing or covering the inlet channel 656, the base 602 completely surrounds and closes the inlet channel 656.

The inlet channel 656 is in fluid communication with the chamber 620 through an inlet ring 660 at least partially below the chamber 620, as shown in the zoomed view of FIG. 6A. More specifically, the inlet ring 660 is at least partially below the chamber channel 628 within the chamber 620. Further, the inlet ring 660 includes holes 662 that are in fluid communication with the chamber 620, and specifically the chamber channel 628. In some aspects, the holes 662 are evenly distributed around the chamber channel 628 to flow fluid into the chamber channel 628 from the inlet ring 660 and, further upstream, from the inlet channel 656. In alternative aspects, the holes 662 may be un-evenly distributed around the chamber channel 628, such as more holes 662 opposite from the inlet channel 656. In some aspects, all of the holes 662 have a uniform diameter. In alternative aspects, the holes 662 have non-uniform diameters, such as the holes 662 opposite from the inlet channel 656 having larger diameters. The positions and diameters of the holes 662 may be configured to provide uniform flow of fluid from the holes 662 throughout the chamber channel 628, or non-uniform flow of fluid from the holes 662 throughout the chamber channel 628. As illustrated, the base 602 does not include an outlet port, a fluid outlet, or an outlet channel. Rather, these features are replaced by a modified lid.

Figure 6B:
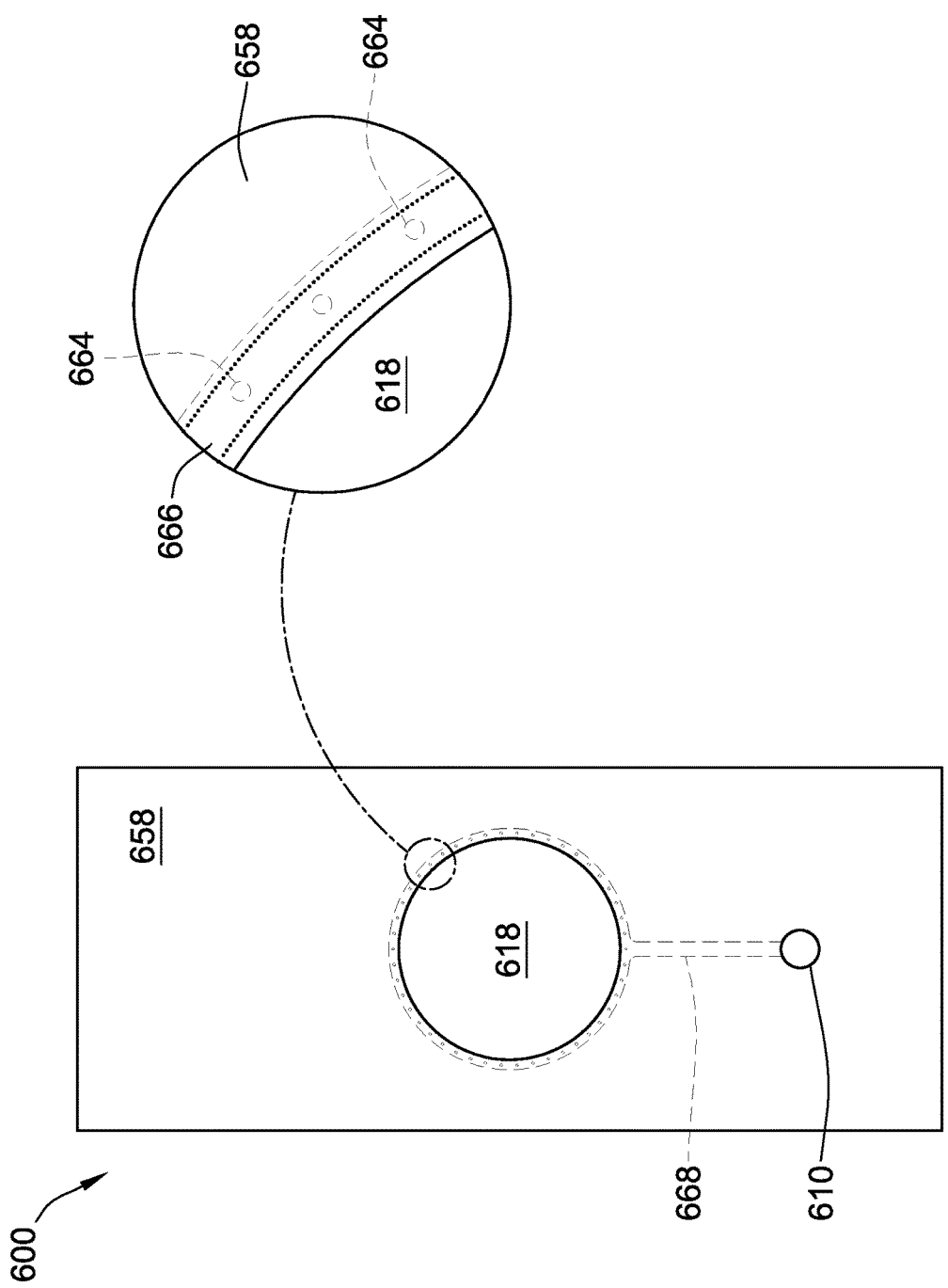
FIG. 6B illustrates a top view of the lid of the radial microfluidic device of FIG. 6A, in accord with some aspects of the present concepts.

FIG. 6B illustrates top view of a modified lid 658 of the device 600 of FIG. 6A, in accord with some aspects of the present concepts. The lid 658 includes holes 664. With the lid 658 on the base 602, the holes 664 are above and aligned with the chamber channel 628. Like the holes 662, the holes 664 can be uniformly or non-uniformly distributed on the lid 604 and aligned with the chamber channel 628. The holes 664 also can have uniform and/or non-uniform diameters.

Further, the lid 658 includes an outlet ring 666. The outlet ring 666 is in fluid communication with the holes 664. The outlet ring 666 further is in fluid communication with an outlet channel 668 within the lid 604. The outlet channel 668 is in fluid communication with an outlet port 610.

Based on the arrangement of the inlet channel 656, the inlet ring 660 having the inlet holes 662, the outlet ring 666 having the outlet holes 664, and the outlet channel 668, fluid can be flowed into the chamber 620, and particularly the chamber channel 628, in a direction parallel with the axis of the chamber 620 (also referred to as axially). Thus, rather than flowing fluid circumferentially within the chamber 620, as described above with respect to the device 100, the device 600 can be configured to flow fluid axially within the chamber 620. The axial flow can simulate similar axial flow across a circular membrane or extracellular scaffold, as may be found in certain biological systems, such as biological systems within the human body, as opposed to circumferential flow.

FIG. 7 illustrates a top view of another alternative radial microfluidic device 700, with the lid not illustrated, in accord with some aspects of the present concepts. The device 700 is generally the same as the device 100 described above. Therefore, like reference numerals correspond to like features. However, the device 700 includes the following differences relative to the device 100. Specifically, radial microfluidic devices as described herein can have more than one chamber channel, more than one chamber ring, and/or more than one chamber well. The device 700 is one of such a varied radial microfluidic device. Like the device 100, the device 700 includes the chamber channel 728 and the chamber well 732. However, the device 700 instead has two chamber rings 730a and 730b. The chamber ring 730a can correspond to the chamber ring 130. To define the chamber ring 730b, the chamber 720 includes additional posts 770 arranged in a ring 770a. The posts 770 are described based on the descriptions provided above for the posts 122 and 124. Thus, like the posts 122 and 124, a combination of the shapes and surface functionalities of the posts 770 and posts 724, in combination with one or more properties of the fluids within the chamber 720 (e.g., between the ring 724a and the ring 770a) constrain the fluid to be within the chamber ring 730b. In some aspects, the chamber rings 730a and 730b, and the chamber well 732 can be concentric relative to each other and relative to the chamber 720. In alterative aspects, one or more (or all) of the chamber rings 730a and 730b and the chamber well 732 can be eccentric relative to one or more of each other and/or relative to the chamber 720.

With both chamber rings 730a and 730a, multiple different types of membranes can be formed, from multiple different fluids having multiple different components therein, such as different cells, different factors, etc. Multiple different membranes can be used together to more accurately mimic structures within a body, such as the human body. For example, a resulting membrane formed within the chamber ring 730a can mimic the porous (spongy) bone layer or compact bone layer of a human bone, and a resulting membrane formed within the chamber ring 730b can mimic the outer membrane (periosteum) of the human bone.

In some aspects, the chamber rings 730a and 730b and the chamber well 732 can be concentric relative to each other and relative to the chamber 720. In alterative aspects, one or more (or all) of the chamber rings 730a and 730b and the chamber well 732 can be eccentric relative to one or more of each other and/or relative to the chamber 720. Further, although only one additional chamber ring is illustrated and described with respect to FIG. 7, more than one additional chamber ring can be added by adding an additional ring of posts. Each additional chamber ring can be concentric and/or eccentric with one or more other chamber rings, and/or the one or more chamber channels and/or one or more chamber wells.

FIG. 8 illustrates a top view of another alternative radial microfluidic device 800, with a lid not illustrated, in accord with some aspects of the present concepts. The device 800 is generally the same as the device 100 described above. Therefore, like reference numerals correspond to like features. However, the device 800 includes the following differences relative to the device 100. Specifically, within the chamber 820 are the chamber channel 828, the chamber ring 830, and the chamber well 832. However, within the chamber well 832 are two smaller wells, namely sample wells 832a and 832b.

To define the sample well 832a, the chamber 820 includes additional posts 872 arranged in a ring 872a. Like the posts 122 and 124 described above, a combination of the shape and surface functionalities of the posts 872, in combination with one or more properties of the fluids within the chamber 820 (e.g., within the ring 872a) constrain fluid to be within the sample well 832a. Similarly, to define the sample well 832b, the chamber 820 includes additional posts 874 arranged in a ring 874a. A combination of the shape and surface functionalities of the posts 874, in combination with one or more properties of the fluids within the chamber 820 (e.g., within the ring 874a) constrain fluid to be within the sample well 832a. Although only two sample wells 832a and 832b are illustrated and described, there may be more than two sample wells within the chamber.

In some aspects, the sample wells 832a and 832b provide points within the chamber 820 for samples of the fluid within the chamber well 832 to be withdrawn. In some aspects, the sample wells 832a and 832b provide areas for investigation subpopulation migrations of cell, as an example. The locations of the sample wells 832a and 832b may vary depending on where from within the gradients formed in the chamber well 832 the samples are withdrawn. In some aspects, the chamber well 832 can be formed of a gelatinous material, which may be hard to remove samples from. In this case, the sample wells 832a and 832b can be made of a less gelatinous material to aid in removing samples therefrom, while still providing a medium for gradients to form.

Further, although two samples chambers are illustrated and described with respect to FIG. 8, only one sample chamber can be added, or more than two sample chambers can be added by adding additional rings of posts. Each additional sample well can be concentric and/or eccentric with one or more other sample wells, and/or the one or more chamber channels and/or one or more chamber rings.

Figure 9:
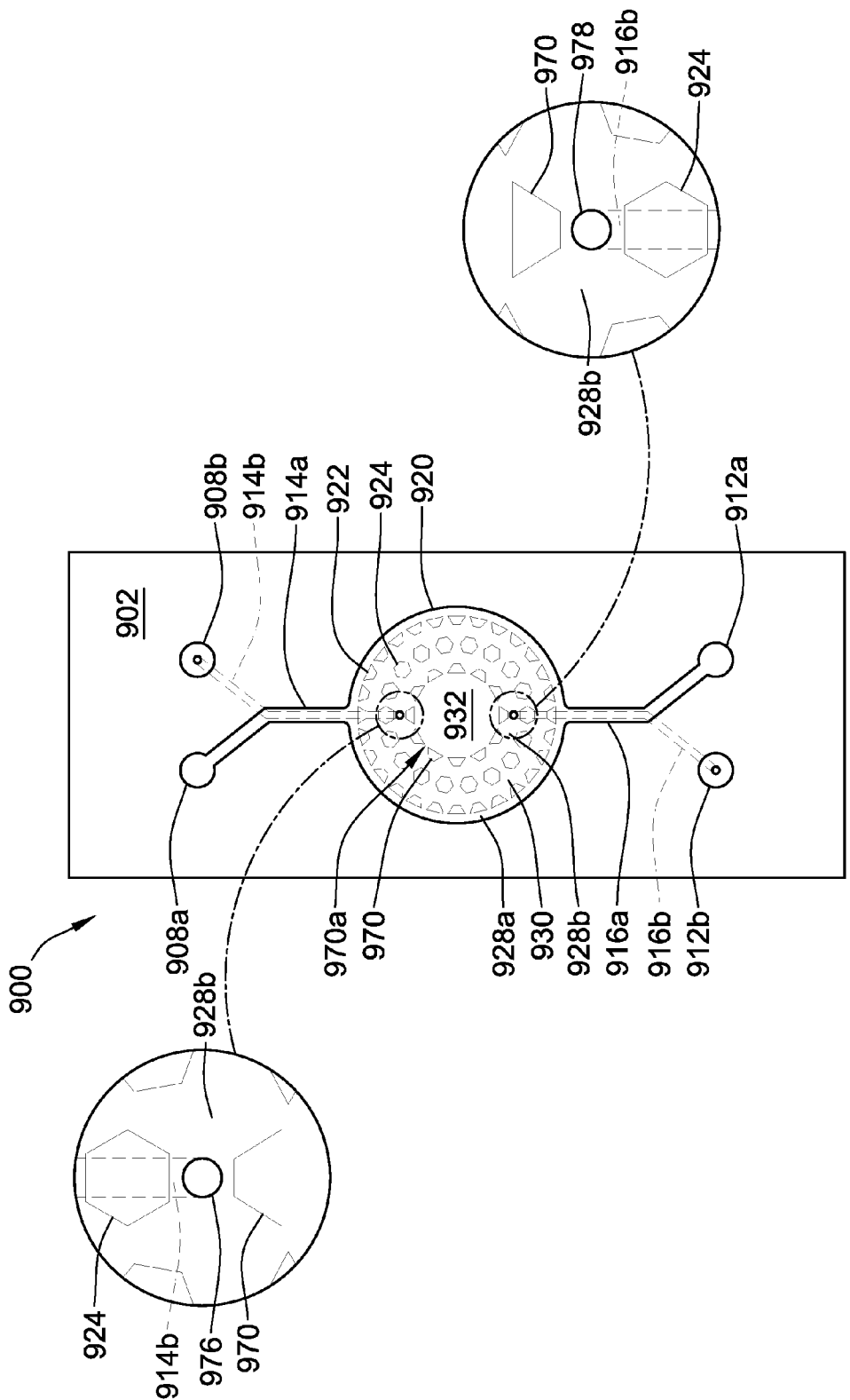
FIG. 9 illustrates a top view of another alternative radial microfluidic device, with a lid removed, in accord with some aspects of the present concepts.

FIG. 9 illustrates a top view of another alternative radial microfluidic device 900, with a lid not illustrated, in accord with some aspects of the present concepts. The device 900 is generally the same as the device 100 described above. Therefore, like reference numerals correspond to like features. However, the base 902 of the device 900 includes fluid inlets 908a and 908b. Each of the fluid inlets 908a and 908b is connected to a separate inlet channel. Specifically, fluid inlet 908a is connected to inlet channel 914a. Fluid inlet 908b is connected to inlet channel 914b. Further, the base 902 of the device 900 includes fluid outlets 912a and 912b.

Each of the fluid outlets 912a and 912b is connected to a separate outlet channel. Specifically, fluid outlet 912a is connected to outlet channel 916a. Fluid outlet 912b is connected to outlet channel 916.

The fluid inlet 908a, the inlet channel 914a, the outlet channel 916a, and the fluid outlet 912a are in fluid communication with the chamber 920 as described above with respect to the fluid inlet 108, the inlet channel 114, the outlet channel 116, and the fluid outlet 112 relative to the chamber 120. However, the fluid inlet 908b, the inlet channel 914b, the outlet channel 916b, and the fluid outlet 912b are in fluid communication with an interior of the chamber 920. Specifically, like the device 700 described above, the chamber 920 of the device 900 includes posts 922, 924, and 970. The wall of the chamber 920 and the posts 922 form the chamber channel 928a. The posts 922 and the posts 924 form the chamber ring 930. The posts 924 and the posts 970 form a second chamber channel, namely the chamber channel 928b. Finally, the posts 970 form the chamber well 932. Thus, although the structure of the posts 970 is similar to the posts 770 of the device 700, the posts 970 define a second chamber channel (chamber channel 928b) as opposed to a channel ring. Specifically, the inlet channel 914b and the outlet channel 916b are in fluid communication with the chamber channel 928b through inlet orifice 976 and outlet orifice 978 within the bottom of the chamber 920, thus allowing fluid to flow into the chamber channel 928b.

The chamber channels 928a and 928b allow for the flow of two different fluids within the chamber 920 within two channels to mimic or approximate more complex biological systems. Fluids having the same fluid matrix with different concentrations of components therein can be flowed through the chamber channels 928a and 928b. Alternatively, different fluids having the same or different concentrations of the same or different components can be flowed through the chamber channels 928a and 928b within different fluid matrixes. The different chamber channels 928a and 928b can be used to introduce into the chamber different cell types, different reagents, etc. to generate different gradients, and can introduce these into different locations of the chamber 920. Further, although two different fluid paths are illustrated and described with the device 900, and particularly the chamber 920, more than two fluid paths can be formed by adding additional combinations of fluid inlets, inlet channels, chamber channels, outlet channels, and fluid outlets.

Although the one or more additional fluid inlets and fluid outlets, the one or more addition inlet channels and outlet channels, the one or more additional chamber channels, the one or more additional chamber rings, or the one or more additional sample chambers are primarily described independent of each other, any combination of these additions can be combined in the same radial microfluidic device. Thus, the same radial microfluidic device can have two or more inlets and outlets, two or more inlet channels and outlet channels, two more chamber channels, two more or more chamber rings, two more or more chamber wells, and/or two more or more sample wells. Further, in some aspects, the same radial microfluidic device can have two more chambers, with each chamber having any combination of the above features. In some aspects, the two more chambers can be in fluid communication with each other in series and/or in parallel. Alternatively, or in addition, two or more radial microfluidic devices, with each one having only one chamber, or any number of chambers, can be arranged in series or in parallel.

The radial microfluidic devices disclosed herein can be used to study and/or model various biological systems and processes, including, for example, bone/bone marrow systems, cancer growth/metastasis, brain layers, neural communications, embryo growth, plant vascular systems, micro/macro-vasculature formation, tumor cell extravasation, and kidney filtration. The radial microfluidic devices can also be used to study bioreactors for synthetic biology/biofuel applications, or whole organism behavior (e.g., C. elegans, planaria, or Xenopus embryos). In some aspects, the radial microfluidic devices can be used as a cell factory, such as the bone-marrow-based production of blood cells. In a similar aspect, the radial microfluidic devices can be used to culture tissue biopsies or explants and promote vascularization. The radial microfluidic devices can also be used to investigate drug resistance development as a result of low-concentration gradients and cell migration, cell differentiation. The radial microfluidic devices can also be used for environmental monitoring or analysis of the impact of environmental conditions, such as nuclear radiation, hormone analogs, heavy metals, chemotherapy, electromagnetic radiation, etc. In some aspects, the radial microfluidic devices can be integrated with electrodes and/or electrode arrays for electrical stimulation or analysis. The radial microfluidic devices also are amenable for ontogenetic stimulation and/or analysis because of the ease of optical access to each compartment based on the translucent and/or removable lid, in addition to any opening within the lid. As discussed above, the radial microfluidic devices can be connected to radial microfluidic devices, including other radial microfluidic devices, within a microfluidic device system. The connections can be through various fluid lines. However, because of the unique nature of the radial microfluidic devices being open, the radial microfluidic devices also can be "connected" to the various other microfluidic devices through sampling or pipetting, such as robotic pipetting.

Although described primarily above with respect to the body, such as the human body, additional uses of the radial microfluidic devices outside of the animal kingdom include the plant kingdom. For example, the radial microfluidic devices can be used for plant root microbiome investigation by growing a plant in the center of the chamber and having the roots spread through the other rings, which could be independently manipulated.

In some aspects, the radial microfluidic devices can include one or more chambers, channels, and/or diaphragms to incorporate stretching or other types of mechanical deformation of the tissues formed within the chambers. The mechanical deformations can be accomplished through external actuation (e.g., vacuum stretching of peripheral channels). Alternatively, or in addition, the mechanical deformations can be accomplished using internal actuation, such as by using magnetic particles embedded within the fluids (e.g., gels) that are influenced by external magnetic fields.

For purposes of the present detailed description, the singular includes the plural and vice versa (unless specifically disclaimed); the words "and" and "or" shall be both conjunctive and disjunctive; the word "all" means "any and all"; the word "any" means "any and all"; and the word "including" means "including without limitation." Additionally, the singular terms "a," "an," and "the" include plural referents unless context clearly indicates otherwise.

While the present invention has been described with reference to one or more particular embodiments, those skilled in the art will recognize that many changes may be made thereto without departing from the spirit and scope of the present invention. Each of these embodiments and obvious variations thereof is contemplated as falling within the spirit and scope of the invention. It is also contemplated that additional embodiments according to aspects of the present invention may combine any number of features from any of the embodiments described herein.

What is claimed is:

1. A method of culturing cells, comprising:
   1) providing a) microfluidic device comprising i) a chamber, said chamber comprising geometric features and a lumen, said lumen covered by ii) a removable lid and in fluidic communication with iii) one or more fluidic channels, b) material capable of forming a gel, and c) cells;
   2) removing said removable lid;
   3) introducing said material under conditions such that a gel forms in said lumen, said gel confined by one or more of said geometric features, and
   4) introducing said cells to said gel, said cells in contact with fluid from said one or more fluidic channels.

2. The method of claim 1, wherein said gel comprises collagen.

3. The method of claim 1, wherein said chamber comprises a round well.

4. The method of claim 1, wherein said geometric features comprise posts.

5. The method of claim 4, wherein said posts comprise a concentric array of posts.

6. The method of claim 1, wherein said cells are cord blood cells.

7. The method of claim 1, wherein
   the gel comprises a first gel confined by at least one of the one or more fluidic channels, said cells comprising first cells within the first gel, the method further comprising:
   providing a second gel comprising second cells in the at least one of the one or more fluidic channels; and
   detecting migration of said first cells toward said second cells.

8. The method of claim 7, wherein said first cells are cord blood cells.

9. The method of claim 7, wherein said second cells are endothelial cells.

10. The method of claim 9, wherein said endothelial cells are human umbilical vein endothelial cells.

11. The method of claim 7, wherein said geometric features comprise posts.

12. The method of claim 11, wherein said posts comprise a concentric array of posts.

* * * * *